US008247170B2

(12) United States Patent
Gygax et al.

(10) Patent No.: US 8,247,170 B2
(45) Date of Patent: Aug. 21, 2012

(54) **DETECTION OF PENICILLIN TOLERANCE IN GROUP B *STREPTOCOCCUS*: SINGLE NUCLEOTIDE POLYMORPHISMS IN PENICILLIN BINDING PROTEIN 4**

(75) Inventors: Scott Elliott Gygax, Bordentown, NJ (US); Aditya Prasad, Marlton, NJ (US); Martin E. Adelson, Belle Mead, NJ (US); Eli Mordechai, Robbinsville, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 377 days.

(21) Appl. No.: 12/454,408

(22) Filed: May 18, 2009

(65) Prior Publication Data
US 2010/0028884 A1 Feb. 4, 2010

Related U.S. Application Data

(60) Provisional application No. 61/127,891, filed on May 16, 2008, provisional application No. 61/190,481, filed on Aug. 29, 2008.

(51) Int. Cl.
*C12Q 1/68* (2006.01)
*C12P 19/34* (2006.01)
*C07H 21/04* (2006.01)
(52) U.S. Cl. ...... 435/6.1; 435/6.11; 435/6.12; 536/24.3; 536/24.33
(58) Field of Classification Search ............ None
See application file for complete search history.

(56) References Cited

U.S. PATENT DOCUMENTS

2006/0160121 A1 * 7/2006 Mounts et al. ............ 435/6
2010/0105865 A1 * 4/2010 Telford et al. ............ 530/350

OTHER PUBLICATIONS

Buck et al., "Design Strategies and Performance of Custom DNA Sequencing Primers," BioTechniques, 1999, vol. 27, pp. 528-536.*
Carl T. Wittwer et al., Continuous Fluorescence Monitoring of Rapid Cycle DNA Amplification, BioTechniques,1997, vol. 22, pp. 130-138.
Yanjiao Zhou et al., Journal of Bacteriology, 2008, vol. 190, pp. 508-514.
Jason P. Trama et al., Moleuclar and Cellular Probes, 2005, vol. 19, pp. 145-152.
Sanjay Tyagi, Red Russell Kramer, Nature Biotechnology, 1996, vol. 14, pp. 303-308.
Kelly C. Rice, Kenneth W. Bayles, Microbiology and Molecular Biology Reveiws, 2008, vol. 72, pp. 85-109.
Pauline Macheboeuf et al., FEMS Microbiol Rev, 2006, vol. 30, pp. 673-691.
Carmen Betriu et al., Antimicrobial Agents and Chemotherapy, 1994, vol. 38, pp. 2183-2186.
P. Sendi, L. Johansson, A. Norrby-Teglund, Infection, 2008, vol. 36, pp. 100-111.
Stephanie Schrag et al., Morbidity and Mortality Weekly Report, 2002, vol. 51, pp. 1-24.
Ronald S. Gibbs, Stephanie Schrag, Anne Schuchat, Obstet Gynecol, 2004, vol. 104, pp. 1062-1076.

* cited by examiner

*Primary Examiner* — Young J Kim
(74) *Attorney, Agent, or Firm* — Siu K. Lo, Esq.

(57) ABSTRACT

Disclosed are methods of detecting penicillin tolerance in Group B *Streptococcus* by detecting at least one of two single nucleotide polymorphisms (SNP) in penicillin binding protein 4. Also disclosed are primers and hybridization probes that may be used in such methods.

27 Claims, 10 Drawing Sheets

BLASTP Analysis of PBP4 comparing a Susceptible and Penicillin Tolerant GBS strains A909 and 2603V/R (Query; Penicillin Susceptible) PBP4 amino acid sequence alignment (blastp) with NEM316 and 515 (Subject; Penicillin Tolerant).

All other PBP4 sequences of penicillin susceptible strains are the same as 2603V/R.

```
Query   1    MPKLIVSFLCILLSLTCVNSVQAEEHKDIMQITREAGYDVKDINKPKASIVIDNKGHILW   60
             MPKLIVSFLCILLSLTCVNSVQAEEHKDIMQITREAGYDVKDINKPKASIVIDNKGHILW
Sbjct   1    MPKLIVSFLCILLSLTCVNSVQAEEHKDIMQITREAGYDVKDINKPKASIVIDNKGHILW   60

Query   61   EDNADLERDPASMSKMFTLYLLFEDLAKGKTSLNTTVTATETDQAISKIYEISNNNIHAG   120
             EDNADLERDPASMSKMFTLYLLFEDLAKGKTSLNTTVTATETDQAISKIYEISNNNIHAG
Sbjct   61   EDNADLERDPASMSKMFTLYLLFEDLAKGKTSLNTTVTATETDQAISKIYEISNNNIHAG   120

Query   121  VAYPIRELITMTAVPSSNVATIMIANHLSQNNPDAFIKRINETAKKLGMTKTHFYNPSGA   180
             VAYPIRELITMTAVPSSNVATIMIANHLSQNNPDAFIKRINETAKKL TKTHFYNPSGA
Sbjct   121  VAYPIRELITMTAVPSSNVATIMIANHLSQNNPDAFIKRINETAKKLDMTKTHFYNPSGA   180

Query   181  VASAFNGLYSPKEYDNNATNVTTARDLSILTYHFLKKYPDILNYTKYPEVKAMVGTPYEE   240
             VASAFNGLYSPKEYDNNATNVTTARDLSILTYHFLKKYPDILNYTKYPEVKAMVGTPYEE
Sbjct   181  VASAFNGLYSPKEYDNNATNVTTARDLSILTYHFLKKYPDILNYTKYPEVKAMVGTPYEE   240

Query   241  TFTTYNYSTPGAKFGLEGVDGLKTGSSPSAAFNALVTAKRQNTRLITVLGVGDWSDQDG   300
             TFTTYNYSTPGAKFGLEGVDGLKTGSSPSAAFNALVTAKRQNTRLITV LGVGDWSDQDG
Sbjct   241  TFTTYNYSTPGAKFGLEGVDGLKTGSSPSAAFNALVTAKRQNTRLITVLGVGDWSDQDG   300

Query   301  EYYRHPFVNALVEKGFKDAKNISSKTPVLKAVKPKKEVTKTKTKSIQEQPQTKEQWWTKT   360
             EYYRHPFVNALVEKGFKDAKNISSKTPVLKAVKPKKEVTKTKTKSIQEQPQTKEQWWTKT
Sbjct   301  EYYRHPFVNALVEKGFKDAKNISSKTPVLKAVKPKKEVTKTKTKSIQEQPQTKEQWWTKT   360

Query   361  DQFIQSHFVSILIVLGTIAILCLLAGIVLLIKRSR   395  (SEQ ID NO: 42)
             DQFIQSHFVSILIVLGTIAILCLLAGIVLLIKRSR        (SEQ ID NO: 43)
Sbjct   361  DQFIQSHFVSILIVLGTIAILCLLAGIVLLIKRSR   395  (SEQ ID NO: 44)
```

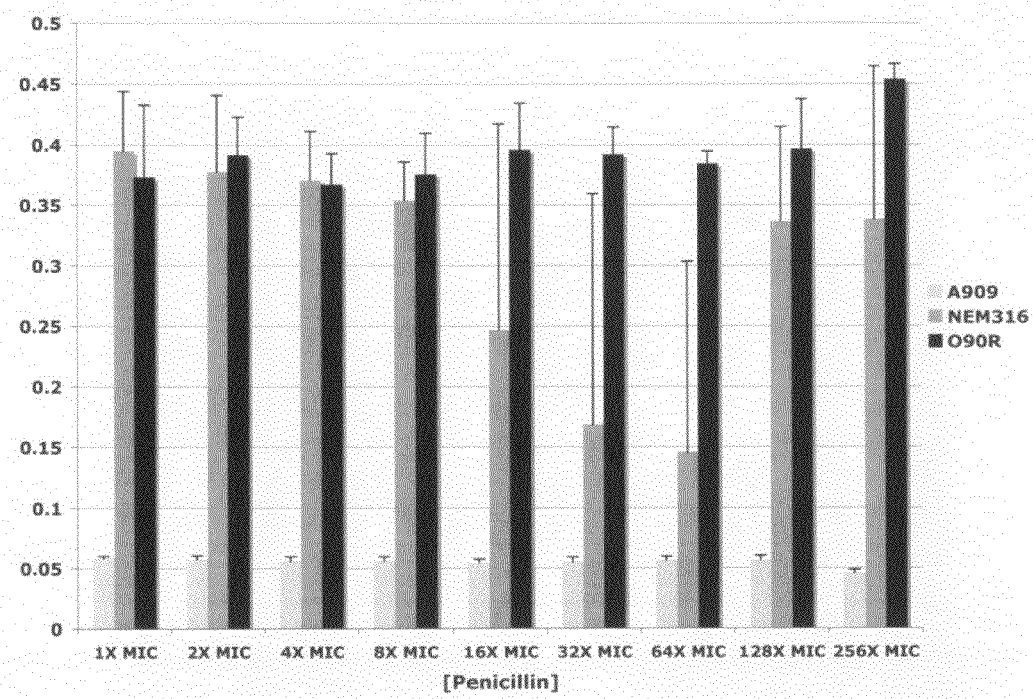
Figure 1    Microbroth Penicillin Tolerance Assay on GBS Laboratory Strains

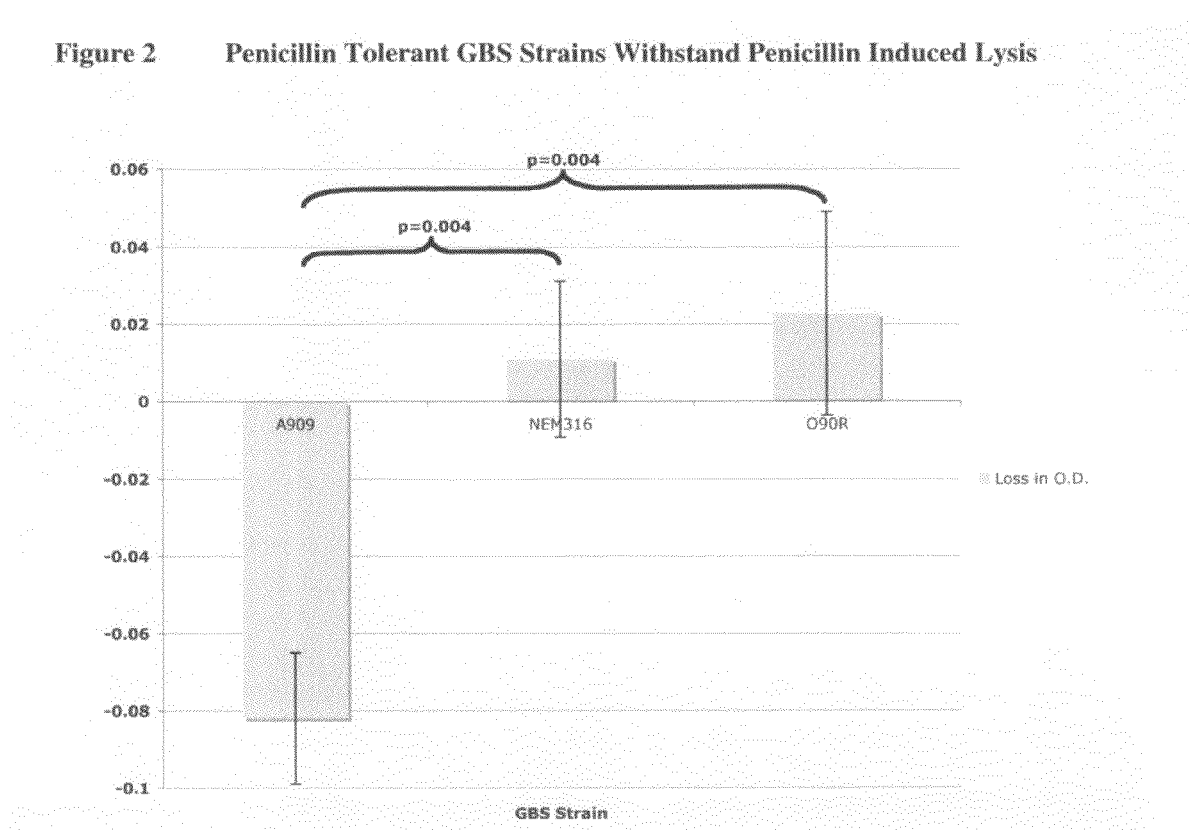
Figure 2  Penicillin Tolerant GBS Strains Withstand Penicillin Induced Lysis

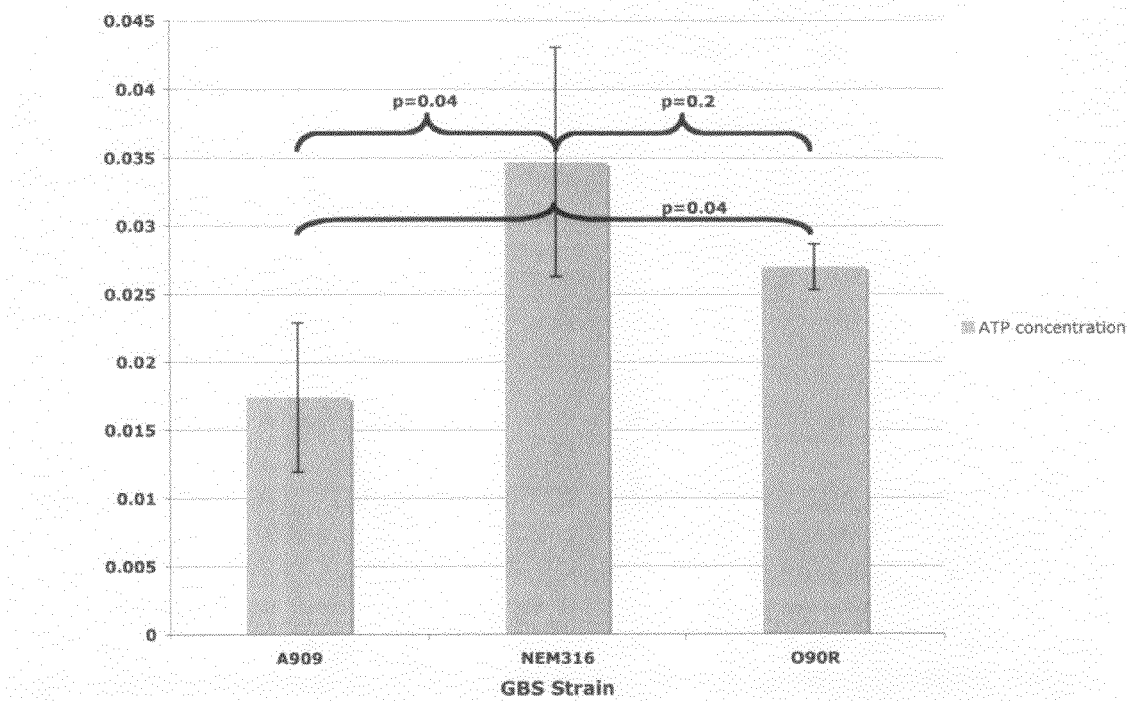
Figure 3    Penicillin Tolerance and Viability Measured by Intracellular [ATP]

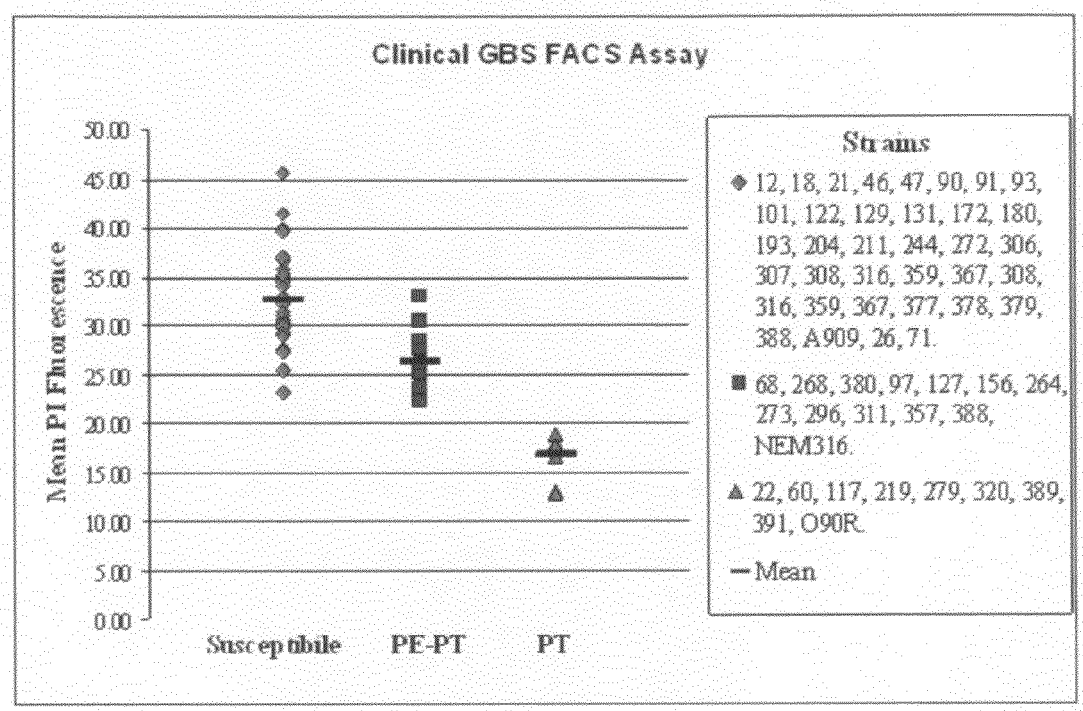
Figure 4  Penicillin Tolerance Assay by Viability Staining and FACS Analysis

Figure 5      BLASTP Analysis of PBP4 comparing a Susceptible and Penicillin Tolerant GBS strains A909 and 2603V/R (Query; Penicillin Susceptible) PBP4 amino acid sequence alignment (blastp) with NEM316 and 515 (Subject; Penicillin Tolerant).

All other PBP4 sequences of penicillin susceptible strains are the same as 2603V/R.

```
Query   1    MPKLIVSFLCILLSLTCVNSVQAEEHKDIMQITREAGYDVKDINKPKASIVIDNKGHILW    60
             MPKLIVSFLCILLSLTCVNSVQAEEHKDIMQITREAGYDVKDINKPKASIVIDNKGHILW
Sbjct   1    MPKLIVSFLCILLSLTCVNSVQAEEHKDIMQITREAGYDVKDINKPKASIVIDNKGHILW    60

Query   61   EDNADLERDPASMSKMFTLYLLFEDLAKGKTSLNTTVTATETDQAISKIYEISNNNIHAG   120
             EDNADLERDPASMSKMFTLYLLFEDLAKGKTSLNTTVTATETDQAISKIYEISNNNIHAG
Sbjct   61   EDNADLERDPASMSKMFTLYLLFEDLAKGKTSLNTTVTATETDQAISKIYEISNNNIHAG   120

Query   121  VAYPIRELITMTAVPSSNVATIMIANHLSQNNPDAFIKRINETAKKLGMTKTHFYNPSGA   180
             VAYPIRELITMTAVPSSNVATIMIANHLSQNNPDAFIKRINETAKKL MTKTHFYNPSGA
Sbjct   121  VAYPIRELITMTAVPSSNVATIMIANHLSQNNPDAFIKRINETAKKLDMTKTHFYNPSGA   180

Query   181  VASAFNGLYSPKEYDNNATNVTTARDLSILTYHFLKKYPDILNYTKYPEVKAMVGTPYEE   240
             VASAFNGLYSPKEYDNNATNVTTARDLSILTYHFLKKYPDILNYTKYPEVKAMVGTPYEE
Sbjct   181  VASAFNGLYSPKEYDNNATNVTTARDLSILTYHFLKKYPDILNYTKYPEVKAMVGTPYEE   240

Query   241  TFTTYNYSTPGAKFGLEGVDGLKTGSSPSAAFNALVTAKRQNTRLITVVLGVGDWSDQDG   300
             TFTTYNYSTPGAKFGLEGVDGLKTGSSPSAAFNALVTAKRQNTRLITV LGVGDWSDQDG
Sbjct   241  TFTTYNYSTPGAKFGLEGVDGLKTGSSPSAAFNALVTAKRQNTRLITVLLGVGDWSDQDG   300

Query   301  EYYRHPFVNALVEKGFKDAKNISSKTPVLKAVKPKKEVTKTKTKSIQEQPQTKEQWWTKT   360
             EYYRHPFVNALVEKGFKDAKNISSKTPVLKAVKPKKEVTKTKTKSIQEQPQTKEQWWTKT
Sbjct   301  EYYRHPFVNALVEKGFKDAKNISSKTPVLKAVKPKKEVTKTKTKSIQEQPQTKEQWWTKT   360

Query   361  DQFIQSHFVSILIVLGTIAILCLLAGIVLLIKRSR   395  (SEQ ID NO: 42)
             DQFIQSHFVSILIVLGTIAILCLLAGIVLLIKRSR        (SEQ ID NO: 43)
Sbjct   361  DQFIQSHFVSILIVLGTIAILCLLAGIVLLIKRSR   395  (SEQ ID NO: 44)
```

Figure 6    Primers used to PCR amplify and sequence identify the SNPs G503A (G168D amino acid polymorphism) and G865A (V289I amino acid polymorphism)

Penicillin binding protein 4 gene sequence from Penicillin Susceptible strain A909 gDNA sequence (NCBI).

(SEQ ID NO: 45)

```
165921
ATACCATACCGTTTAATGAGATTCATAATTCACAGGTTGCTTTAGAGCATGAAGCAAAGGTGTCTAAGAT
TTCTGAAGAGCAACTGTACTACTTGATGAGTCGAGGTTTATCTGAAGCTGAGGCAACAGAAATGATTGTT
ATGGGGTTTGTTGAGCCCTTTACGAAAGAATTACCAATGGAATATGCGGTAGAGTTAAACCGCTTAATTT
CCTATGAAATGGAAGGTTCAGTTGGTTAATTGAAGATTTCAAGAGATAATAAAAAGCCCCTATGTTATTG
                                         [STOP]
ATGAAGGGGGCTTTTATATTAGCACAGTTATTATCTAGAGCGCTTTATAAGTAATACTATCCCAGCTAAAA
GACAAAGGATAGCGATGGTGCCCAGAACAATTAAAATAGATACAAAATGTGATTGAATAAATTGATCTGTT
TTTGTCCACCACTGTTCTTTTGTTTGAGGCTGTTCTTGAATAGATTTGGTTTTGGTTTTAGTAACTTCTTT
        PBP4-AP4>>>>>>>>>>>>>>>>
TTTAGGTTTAACGGCTTTTAATACAGGAGTTTTAGAAGAAATATTTTTAGCGTCTTTAAAACCTTTTTCTA
                                                                V289I
CAAGAGCGTTGACAAACGGATGACGATAGTACTCTCCGTCTTGGTCTGACCAATCACCAACTCCTAAAACC
ACAGTTATCAAGCGAGTATTCTGGCGTTTAGCTGTAACTAAGGCATTAAAAGCAGCGCTAGGGCTAGAACC
AGTTTTTAAGCCATCTACTCCTTCTAATCCAAATTTAGCGCCGGGGGTAGAGTAGTTATAAGTTGTAAATG
       <<<<<<<<<<<PBP4-AP3
TTTCTTCATAAGGAGTTCCGACCATGGCCTTGACTTCAGGATATTTTGTATAGTTCAGTATATCAGGGTAT
                                                PBP4-AP1>>>>>>>>>>>
TTTTTAAGGAAATGATAGGTTAAAATTGATAGATCACGTGCAGTCGTAACGTTAGTAGCATTGTTATCGTA
TTCTTTTGGGGAGTAAAGTCCATTAAAAGCACTCGCTACCGCCCCACTGGGGTTATAAAAGTGAGTTTTTG
      G168D
TCATACCGAGTTTCTTGGCGGTTTCATTGATTCGTTTAATGAAGGCGTCAGGATTGTTTTGTGATAAGTGG
                                              <<<<<<<<<<<PBP4-AP2
TTAGCAATCATAATAGTTGCTACATTAGATGACGGGACAGCTGTCATAGTAATCAGTTCACGAATAGGATA
AGCAACCCCAGCATGAATATTATTATTACTAATTTCATAAATCTTACTTATGGCTTGGTCTGTTTCTGTTG
CAGTCACTGTGGTGTTGAGGCTTGTTTTTCCTTTAGCTAAGTCTTCAAATAGTAAATATAAAGTAAACATT
TTAGACATGCTAGCGGGATCACGTTCTAAATCAGCGTTATCTTCCCACAAAATATGACCTTTATTGTCAAT
AACGATAGACGCTTTAGGTTTATTAATATCTTTAACATCATATCCGGCTTCTCGGGTAATTTGCATAATAT
CTTTATGTTCTTCAGCTTGCACAGAGTTTACACAAGTCAGGGATAATAAAATGCAGAGGAAAGATACGATT
        [START]
AATTTAGGCATAGGTAACTCCTGAAAACTTTTTATTAATATTATAACAAAAAATCACTAATAAAAAGACA
TTTCATTAGTGATTTTTAATTTTATATATTCTCCTAAACCTAGCTAAAGAAACTGCTGTGCAGCAACTCCT
TGTGTCAAAGGGAGATTACTATTAAAGTTTTTCGTTAACGTAGCGCACAAAATGATTCCACCACACTTTGA
GGAAGAAACTGCGCTCAATACTATCTTTTGCCACTAAATGAACGCTAGGTTCCTTTATGAGATAGCCTTTT
                                                                167691
```

Figure 7    Primers and hybridization probe used in the Penicillin Tolerance Real-Time PCR Assay for SNP G503A

Penicillin binding protein 4 gene sequence from Penicillin Tolerant strain NEM316 gDNA sequence (NCBI).

(SEQ ID NO: 46)

NC_004368. *Streptococcus agalactiae*...[gi:25010075]
GeneID: 1031213

[START]
```
ATGCCTAAAT TAATCGTATC TTTCCTCTGC ATTTTATTAT CCCTGACTTG TGTAAACTCT
GTGCAAGCTG AAGAACATAA AGATATTATG CAAATTACCC GAGAAGCCGG ATATGATGTT
AAAGATATTA ATAAACCTAA AGCGTCTATC GTTATTGACA ATAAAGGTCA TATTTTGTGG
GAAGATAACG CTGATTTAGA ACGTGATCCC GCTAGCATGT CTAAAATGTT TACTTTATAT
TTACTATTTG AAGACTTAGC TAAAGGAAAA ACAAGCCTCA ACACCACAGT GACTGCAACA
GAAACAGACC AAGCCATAAG TAAGATTTAT GAAATTAGTA ATAACAATAT TCATGCTGGG
                                                PBP4-F2>>>>>>>>>>>>>>>
PBP4-F1>>>>>>>>>>>>>>>>>>>                      PBP4-F3>>>>>>>>>>>>>>>>
GTTGCTTATC CTATTCGTGA ACTGATTACT ATGACGGCTG TCCCGTCATC TAATGTAGCA
```

```
                PBP4-F4>>>>>>>>>>>>>
ACTATTATGA TTGCTAACCA CTTATCACAA AACAATCCTG ACGCCTTCAT TAAACGAATC
```

```
              Hybridization Probe
AATGAAACCG CCAAGAAACT CGATATGACA AAAACTCACT TTTATAACCC TAGTGGGGCG
```

```
                                           <<<<<<<<<<<<<<<<<PBP4-R1
             <<<<<<<<<<<<<<<<<<<PBP4-R3        <<<<<<<<<<<<<
GTAGCAAGTG CTTTTAATGG ACTTTACTCC CCAAAAGAAT ACGATAACAA TGCTACTAAC
<PBP4-R2 <<<<<<<<<<<<<<<<<<<<PBP4-R4
GTTACGACTG CACGTGATCT ATCAATTTTA ACCTATCATT TCCTTAAAAA ATACCCTGAT
ATACTGAACT ATACAAAATA TCCTGAAGTC AAGGCCATGG TCGGAACTCC TTATGAAGAA
ACATTTACAA CTTATAACTA CTCTACCCCC GGCGCTAAAT TTGGATTAGA AGGAGTAGAT
GGCTTAAAAA CTGGTTCTAG CCCTAGCGCT GCTTTTAATG CCTTAGTTAC AGCTAAACGC
CAGAATACTC GTTTGATAAC TGTGATTTTA GGCGTTGGCG ATTGGTCAGA CCAAGACGGA
GAGTACTATC GTCATCCGTT TGTCAACGCT CTTGTAGAAA AAGGTTTTAA AGACGCTAAA
AATATTTCTT CTAAAACTCC TGTATTAAAA GCCGTTAAAC CTAAAAAAGA AGTTACTAAA
ACCAAAACCA AATCTATTCA AGAACAGCCT CAAACAAAAG AACAGTGGTG GACAAAAACA
GATCAATTTA TTCAATCACA TTTTGTATCT ATTTTAATTG TTCTGGGAAC CATCGCTATC
CTTTGTCTTT TAGCTGGGAT AGTATTACTT ATAAAGCGCT CTAGATAA [STOP]
```

Figure 8 **The Effects of *pbp4* Allele Replacement in A909 and O90R on Membrane Permeability and Cell Viability. Cells are grown to O.D.$_{600}$ of 0.25 followed by penicillin treatment (100x MIC$_{90}$) for 48 h. The cells are then stained with (a)10 µM Propidium iodide (PI) or (b**) 0.25 µM RedoxSensor Green (RSG) and fixed with 4% paraformaldehyde in PBS. The mean fluorescence intensity was determined from 50,000 events in each sample by FACS analysis. The A909 (S strain) *pbp4*-GV allele and O90R (PT strain) *pbp4*-DI allele derivatives were integrated with the opposing allele (GV to DI or DI to GV) or the same allele (GV to GV or DI to DI) as a control.

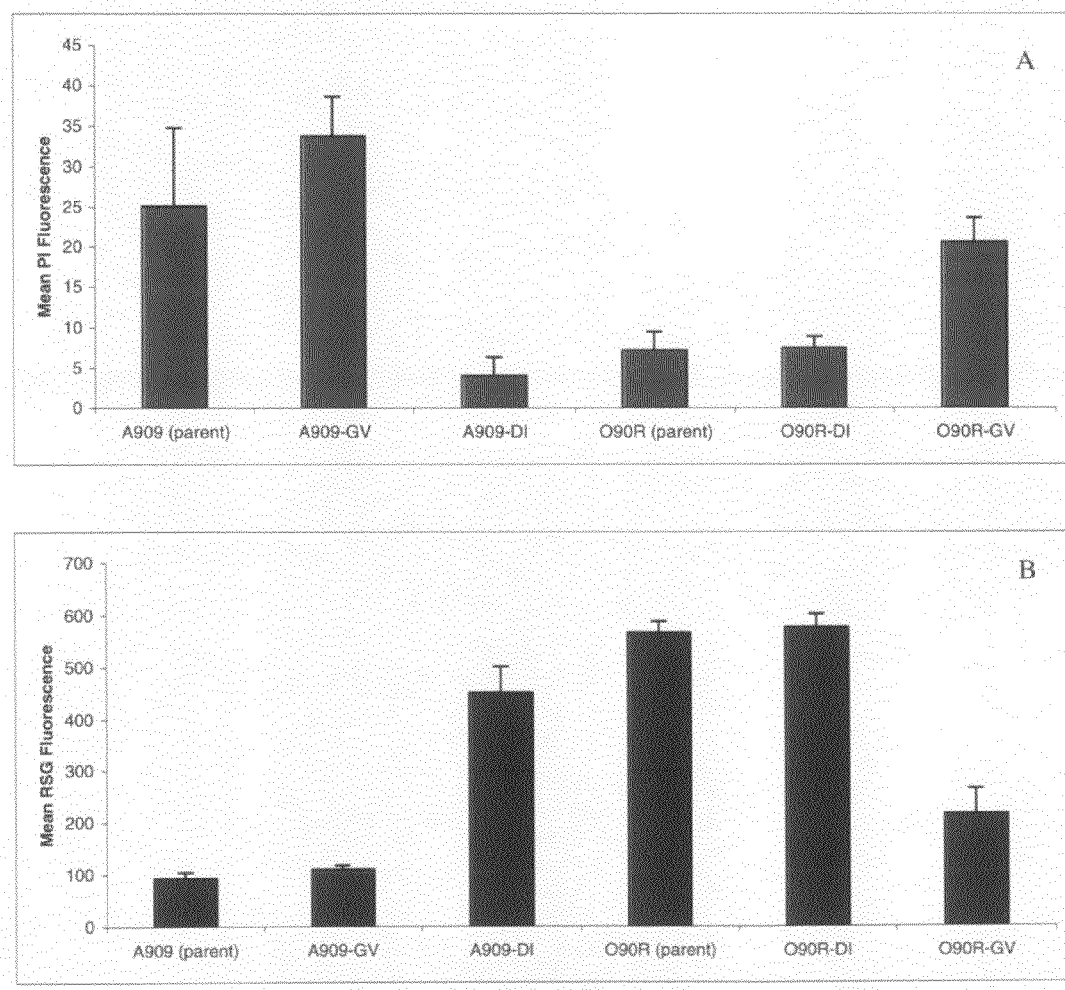

Figure 9 The Effects of *pbp4* Allele Replacement in A909 and O90R on Cell Viability. Cells are grown to $OD_{600}$ of 0.25 followed by penicillin treatment (100x $MIC_{90}$) for 48 h. A survival assay was used to assess cell wall integrity upon cell wall digestive enzyme treatment. Cells of allele replaced and their corresponding control strains were treatment with lysozyme and mutanolysin (Final enzyme concentration of 5 µg/ml each) for 0, 30, 60, 90 and 120 minutes at 37°C. Cell counts were performed to determine % survival of 100ul aliquots of each after overnight incubation at 37°C on TSB plates.

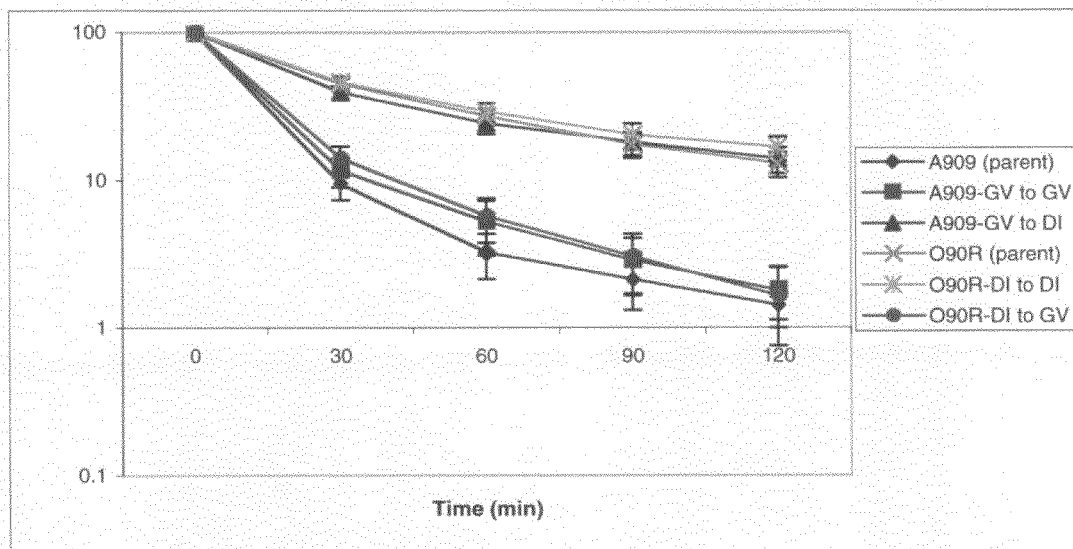

**Figure 10. The effects of *pbp4* allele replacement in A909 and O90R on cell wall integrity.** Cells are grown to O.D.$_{600}$ of 0.25 followed by penicillin treatment (100x MIC$_{90}$) for 48 h. Isolated peptidoglycan cross-linkage was treated with lysozyme and mutanolysin. Muropeptide composition and digestion patterns of peptidoglycan purified form the susceptible (S) parent (A909), penicillin tolerant (PT) parent (O90R), S allele-replacement control (A909-GV), PT allele-replacement control (O90R-DI), S to PT allele replacement (A909-DI), and PT to S allele replacement (O90R-GV) GBS strains were (M; molecular weight markers). The peptidoglycan layer was isolated from the cells and digested with lysozyme and mutanolysin (5 µg/ml of each) for 16 h at 37°C. Insoluble material was removed by centrifugation and 15 µg of the solubilized peptidoglycan fragments of each sample was run on a 16.5% tris-tricine peptide gel.

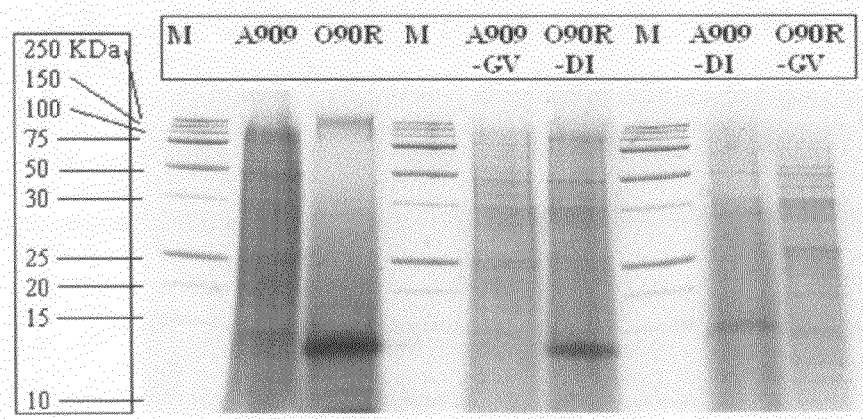

SEQUENCE LISTING

```
<160> NUMBER OF SEQ ID NOS: 46

<210> SEQ ID NO 1
<211> LENGTH: 19
<212> TYPE: DNA
<213> ORGANISM: Streptococcus agalactiae

<400> SEQUENCE: 1
cagtcgtaac gttagtagc                                                  19

<210> SEQ ID NO 2
<211> LENGTH: 23
<212> TYPE: DNA
<213> ORGANISM: Streptococcus agalactiae

<400> SEQUENCE: 2
ggcttttaat acaggagttt tag                                             23

<210> SEQ ID NO 3
<211> LENGTH: 20
<212> TYPE: DNA
<213> ORGANISM: Streptococcus agalactiae

<400> SEQUENCE: 3
cctattcgtg aactgattac                                                 20

<210> SEQ ID NO 4
<211> LENGTH: 20
<212> TYPE: DNA
```

<213> ORGANISM: Streptococcus agalactiae

<400> SEQUENCE: 4
ggtcggaact ccttatgaag                    20

<210> SEQ ID NO 5
<211> LENGTH: 23
<212> TYPE: DNA
<213> ORGANISM: Streptococcus agalactiae

<400> SEQUENCE: 5
ttgcttatcc tattcgtgaa ctg                23

<210> SEQ ID NO 6
<211> LENGTH: 19
<212> TYPE: DNA
<213> ORGANISM: Streptococcus agalactiae

<400> SEQUENCE: 6
ctgtcccgtc atctaatgt                     19

<210> SEQ ID NO 7
<211> LENGTH: 21
<212> TYPE: DNA
<213> ORGANISM: Streptococcus agalactiae

<400> SEQUENCE: 7
gtcccgtcat ctaatgtagc a                  21

<210> SEQ ID NO 8
<211> LENGTH: 19
<212> TYPE: DNA
<213> ORGANISM: Streptococcus agalactiae

<400> SEQUENCE: 8
caatcctgac gccttcatt                     19

<210> SEQ ID NO 9
<211> LENGTH: 25
<212> TYPE: DNA
<213> ORGANISM: Streptococcus agalactiae

<400> SEQUENCE: 9
cgttagtagc attgttatcg tattc              25

<210> SEQ ID NO 10
<211> LENGTH: 22
<212> TYPE: DNA
<213> ORGANISM: Streptococcus agalactiae

<400> SEQUENCE: 10
gtcgtaacgt tagtagcatt gt                 22

<210> SEQ ID NO 11
<211> LENGTH: 24
<212> TYPE: DNA
<213> ORGANISM: Streptococcus agalactiae

<400> SEQUENCE: 11
cttttgggga gtaaagtcca ttaa               24

<210> SEQ ID NO 12
<211> LENGTH: 24
<212> TYPE: DNA

<213> ORGANISM: Streptococcus agalactiae

<400> SEQUENCE: 12
ggttaaaatt gatagatcac gtgc  24

<210> SEQ ID NO 13
<211> LENGTH: 24
<212> TYPE: DNA
<213> ORGANISM: Streptococcus agalactiae

<400> SEQUENCE: 13
cgccaagaaa ctcgatatga caaa  24

<210> SEQ ID NO 14
<211> LENGTH: 24
<212> TYPE: DNA
<213> ORGANISM: Streptococcus agalactiae

<400> SEQUENCE: 14
tttgtcatat cgagtttctt ggcg  24

<210> SEQ ID NO 15
<211> LENGTH: 23
<212> TYPE: DNA
<213> ORGANISM: Streptococcus agalactiae

<400> SEQUENCE: 15
gccaagaaac tcggtatgac aaa  23

<210> SEQ ID NO 16
<211> LENGTH: 23
<212> TYPE: DNA
<213> ORGANISM: Streptococcus agalactiae

<400> SEQUENCE: 16
tttgtcatac cgagtttctt ggc  23

<210> SEQ ID NO 17
<211> LENGTH: 20
<212> TYPE: DNA
<213> ORGANISM: Streptococcus agalactiae

<400> SEQUENCE: 17
ctggaactct agtggctggt  20

<210> SEQ ID NO 18
<211> LENGTH: 24
<212> TYPE: DNA
<213> ORGANISM: Streptococcus agalactiae

<400> SEQUENCE: 18
catttgctgg gcttgattat tact  24

<210> SEQ ID NO 19
<211> LENGTH: 16
<212> TYPE: DNA
<213> ORGANISM: Streptococcus agalactiae

<400> SEQUENCE: 19
agtgacaact ccacaa  16

<210> SEQ ID NO 20
<211> LENGTH: 19
<212> TYPE: DNA

```
<213> ORGANISM: Streptococcus agalactiae

<400> SEQUENCE: 20
caagagataa taaaaagcc                                                  19

<210> SEQ ID NO 21
<211> LENGTH: 25
<212> TYPE: DNA
<213> ORGANISM: Streptococcus agalactiae

<400> SEQUENCE: 21
taacctaaat taatcgtatc tttcc                                           25

<210> SEQ ID NO 22
<211> LENGTH: 22
<212> TYPE: DNA
<213> ORGANISM: Streptococcus agalactiae

<400> SEQUENCE: 22
gaattaccaa tggaatatgc gg                                              22

<210> SEQ ID NO 23
<211> LENGTH: 20
<212> TYPE: DNA
<213> ORGANISM: Streptococcus agalactiae

<400> SEQUENCE: 23
cagataggcc taatgactgg                                                 20

<210> SEQ ID NO 24
<211> LENGTH: 14
<212> TYPE: PRT
<213> ORGANISM: Streptococcus agalactiae

<400> SEQUENCE: 24

Thr Ala Lys Lys Leu Gly Met Thr Lys Thr His Phe Tyr Asn
1               5                   10

<210> SEQ ID NO 25
<211> LENGTH: 13
<212> TYPE: PRT
<213> ORGANISM: Streptococcus agalactiae

<400> SEQUENCE: 25

Thr Arg Leu Ile Thr Val Val Leu Gly Val Gly Asp Trp
1               5                   10

<210> SEQ ID NO 26
<211> LENGTH: 14
<212> TYPE: PRT
<213> ORGANISM: Streptococcus agalactiae

<400> SEQUENCE: 26

Thr Ala Lys Lys Leu Asp Met Thr Lys Thr His Phe Tyr Asn
1               5                   10

<210> SEQ ID NO 27
<211> LENGTH: 13
<212> TYPE: PRT
<213> ORGANISM: Streptococcus agalactiae

<400> SEQUENCE: 27

Thr Arg Leu Ile Thr Val Ile Leu Gly Val Gly Asp Trp
1               5                   10
```

```
<210> SEQ ID NO 28
<211> LENGTH: 14
<212> TYPE: PRT
<213> ORGANISM: Streptococcus pyogenes

<400> SEQUENCE: 28

Thr Ala Lys Gln Leu Gly Met Thr Asn Thr His Phe Ser Asn
1               5                   10

<210> SEQ ID NO 29
<211> LENGTH: 13
<212> TYPE: PRT
<213> ORGANISM: Streptococcus pyogenes

<400> SEQUENCE: 29

Thr Arg Leu Ile Thr Ile Val Met Gly Val Gly Asp Trp
1               5                   10

<210> SEQ ID NO 30
<211> LENGTH: 14
<212> TYPE: PRT
<213> ORGANISM: Enterococcus faecalis

<400> SEQUENCE: 30

Lys Ala Ala Glu Leu Gly Met Thr Asn Thr Thr Tyr Tyr Asn
1               5                   10

<210> SEQ ID NO 31
<211> LENGTH: 13
<212> TYPE: PRT
<213> ORGANISM: Enterococcus faecalis

<400> SEQUENCE: 31

Phe Arg Leu Ile Glu Val Ile Leu Gly Val Gly Asn Trp
1               5                   10

<210> SEQ ID NO 32
<211> LENGTH: 14
<212> TYPE: PRT
<213> ORGANISM: Staphylococcus aureus

<400> SEQUENCE: 32

Lys Ala Lys Ala Ile Gly Met Lys Asn Thr His Phe Val Asn
1               5                   10

<210> SEQ ID NO 33
<211> LENGTH: 13
<212> TYPE: PRT
<213> ORGANISM: Staphylococcus aureus

<400> SEQUENCE: 33

Phe Arg Ile Asn Gln Val Ile Met Gly Ala Gly Asp Tyr
1               5                   10

<210> SEQ ID NO 34
<211> LENGTH: 14
<212> TYPE: PRT
<213> ORGANISM: Streptomyces sp.

<400> SEQUENCE: 34

Ala Ala Thr Asn Leu Gly Leu His Asn Thr His Phe Asp Ser
1               5                   10

<210> SEQ ID NO 35
<211> LENGTH: 13
```

```
<212> TYPE: PRT
<213> ORGANISM: Streptomyces sp.

<400> SEQUENCE: 35

Lys Thr Val Ile Gly Thr Val Leu Ala Ser Thr Ser Ile
 1               5                  10

<210> SEQ ID NO 36
<211> LENGTH: 14
<212> TYPE: PRT
<213> ORGANISM: Escherichia coli

<400> SEQUENCE: 36

Tyr Val Asn Ala Leu Gly Leu Lys Asn Thr His Phe Gln Thr
 1               5                  10

<210> SEQ ID NO 37
<211> LENGTH: 13
<212> TYPE: PRT
<213> ORGANISM: Escherichia coli

<400> SEQUENCE: 37

Met Arg Leu Ile Ser Ala Val Met Gly Gly Arg Thr Phe
 1               5                  10

<210> SEQ ID NO 38
<211> LENGTH: 14
<212> TYPE: PRT
<213> ORGANISM: Bacillus subtilis

<400> SEQUENCE: 38

Lys Ala Lys Glu Leu Gly Leu Lys Asn Thr Ser Phe Lys Asn
 1               5                  10

<210> SEQ ID NO 39
<211> LENGTH: 13
<212> TYPE: PRT
<213> ORGANISM: Bacillus subtilis

<400> SEQUENCE: 39

Met Arg Ala Ile Ala Val Val Phe Gly Ala Ser Thr Pro
 1               5                  10

<210> SEQ ID NO 40
<211> LENGTH: 14
<212> TYPE: PRT
<213> ORGANISM: Pseudomonas aeruginosa

<400> SEQUENCE: 40

Lys Ala His Ala Leu Gly Met Lys Asn Thr Arg Tyr Val Glu
 1               5                  10

<210> SEQ ID NO 41
<211> LENGTH: 13
<212> TYPE: PRT
<213> ORGANISM: Pseudomonas aeruginosa

<400> SEQUENCE: 41

Ser Pro Val Asn Leu Val Val Leu Asp Ala Phe Gly Lys
 1               5                  10

<210> SEQ ID NO 42
<211> LENGTH: 395
<212> TYPE: PRT
<213> ORGANISM: Streptococcus agalactiae
```

<400> SEQUENCE: 42

```
Met Pro Lys Leu Ile Val Ser Phe Leu Cys Ile Leu Leu Ser Leu Thr
 1               5                  10                  15
Cys Val Asn Ser Val Gln Ala Glu Glu His Lys Asp Ile Met Gln Ile
            20                  25                  30
Thr Arg Glu Ala Gly Tyr Asp Val Lys Asp Ile Asn Lys Pro Lys Ala
        35                  40                  45
Ser Ile Val Ile Asp Asn Lys Gly His Ile Leu Trp Glu Asp Asn Ala
    50                  55                  60
Asp Leu Glu Arg Asp Pro Ala Ser Met Ser Lys Met Phe Thr Leu Tyr
65                  70                  75                  80
Leu Leu Phe Glu Asp Leu Ala Lys Gly Lys Thr Ser Leu Asn Thr Thr
                85                  90                  95
Val Thr Ala Thr Glu Thr Asp Gln Ala Ile Ser Lys Ile Tyr Glu Ile
            100                 105                 110
Ser Asn Asn Asn Ile His Ala Gly Val Ala Tyr Pro Ile Arg Glu Leu
        115                 120                 125
Ile Thr Met Thr Ala Val Pro Ser Ser Asn Val Ala Thr Ile Met Ile
    130                 135                 140
Ala Asn His Leu Ser Gln Asn Asn Pro Asp Ala Phe Ile Lys Arg Ile
145                 150                 155                 160
Asn Glu Thr Ala Lys Lys Leu Gly Met Thr Lys Thr His Phe Tyr Asn
                165                 170                 175
Pro Ser Gly Ala Val Ala Ser Ala Phe Asn Gly Leu Tyr Ser Pro Lys
            180                 185                 190
Glu Tyr Asp Asn Asn Ala Thr Asn Val Thr Thr Ala Arg Asp Leu Ser
        195                 200                 205
Ile Leu Thr Tyr His Phe Leu Lys Lys Tyr Pro Asp Ile Leu Asn Tyr
    210                 215                 220
Thr Lys Tyr Pro Glu Val Lys Ala Met Val Gly Thr Pro Tyr Glu Glu
225                 230                 235                 240
Thr Phe Thr Thr Tyr Asn Tyr Ser Thr Pro Gly Ala Lys Phe Gly Leu
                245                 250                 255
Glu Gly Val Asp Gly Leu Lys Thr Gly Ser Ser Pro Ser Ala Ala Phe
            260                 265                 270
Asn Ala Leu Val Thr Ala Lys Arg Gln Asn Thr Arg Leu Ile Thr Val
        275                 280                 285
Val Leu Gly Val Gly Asp Trp Ser Asp Gln Asp Gly Glu Tyr Tyr Arg
    290                 295                 300
His Pro Phe Val Asn Ala Leu Val Glu Lys Gly Phe Lys Asp Ala Lys
305                 310                 315                 320
Asn Ile Ser Ser Lys Thr Pro Val Leu Lys Ala Val Lys Pro Lys Lys
                325                 330                 335
Glu Val Thr Lys Thr Lys Thr Lys Ser Ile Glu Glu Pro Gln Thr
            340                 345                 350
Lys Glu Gln Trp Trp Thr Lys Thr Asp Gln Phe Ile Gln Ser His Phe
        355                 360                 365
Val Ser Ile Leu Ile Val Leu Gly Thr Ile Ala Ile Leu Cys Leu Leu
    370                 375                 380
Ala Gly Ile Val Leu Leu Ile Lys Arg Ser Arg
385                 390                 395
```

<210> SEQ ID NO 43
<211> LENGTH: 393

<212> TYPE: PRT
<213> ORGANISM: Streptococcus agalactiae

<400> SEQUENCE: 43

```
Met Pro Lys Leu Ile Val Ser Phe Leu Cys Ile Leu Ser Leu Thr
 1               5                  10                  15

Cys Val Asn Ser Val Gln Ala Glu Glu His Lys Asp Ile Met Gln Ile
            20                  25                  30

Thr Arg Glu Ala Gly Tyr Asp Val Lys Asp Ile Asn Lys Pro Lys Ala
        35                  40                  45

Ser Ile Val Ile Asp Asn Lys Gly His Ile Leu Trp Glu Asp Asn Ala
    50                  55                  60

Asp Leu Glu Arg Asp Pro Ala Ser Met Ser Lys Met Phe Thr Leu Tyr
 65                  70                  75                  80

Leu Leu Phe Glu Asp Leu Ala Lys Gly Lys Thr Ser Leu Asn Thr Thr
                85                  90                  95

Val Thr Ala Thr Glu Thr Asp Gln Ala Ile Ser Lys Ile Tyr Glu Ile
                100                 105                 110

Ser Asn Asn Asn Ile His Ala Gly Val Ala Tyr Pro Ile Arg Glu Leu
            115                 120                 125

Ile Thr Met Thr Ala Val Pro Ser Ser Asn Val Ala Thr Ile Met Ile
        130                 135                 140

Ala Asn His Leu Ser Gln Asn Asn Pro Asp Ala Phe Ile Lys Arg Ile
145                 150                 155                 160

Asn Glu Thr Ala Lys Lys Leu Met Thr Lys Thr His Phe Tyr Asn Pro
                165                 170                 175

Ser Gly Ala Val Ala Ser Ala Phe Asn Gly Leu Tyr Ser Pro Lys Glu
            180                 185                 190

Tyr Asp Asn Asn Ala Thr Asn Val Thr Thr Ala Arg Asp Leu Ser Ile
        195                 200                 205

Leu Thr Tyr His Phe Leu Lys Lys Tyr Pro Asp Ile Leu Asn Tyr Thr
    210                 215                 220

Lys Tyr Pro Glu Val Lys Ala Met Val Gly Thr Pro Tyr Glu Glu Thr
225                 230                 235                 240

Phe Thr Thr Tyr Asn Tyr Ser Thr Pro Gly Ala Lys Phe Gly Leu Glu
                245                 250                 255

Gly Val Asp Gly Leu Lys Thr Gly Ser Ser Pro Ser Ala Ala Phe Asn
            260                 265                 270

Ala Leu Val Thr Ala Lys Arg Gln Asn Thr Arg Leu Ile Thr Val Leu
        275                 280                 285

Gly Val Gly Asp Trp Ser Asp Gln Asp Gly Glu Tyr Tyr Arg His Pro
    290                 295                 300

Phe Val Asn Ala Leu Val Glu Lys Gly Phe Lys Asp Ala Lys Asn Ile
305                 310                 315                 320

Ser Ser Lys Thr Pro Val Leu Lys Ala Val Lys Pro Lys Lys Glu Val
                325                 330                 335

Thr Lys Thr Lys Thr Lys Ser Ile Gln Glu Gln Pro Gln Thr Lys Glu
            340                 345                 350

Gln Trp Trp Thr Lys Thr Asp Gln Phe Ile Gln Ser His Phe Val Ser
        355                 360                 365

Ile Leu Ile Val Leu Gly Thr Ile Ala Ile Leu Cys Leu Leu Ala Gly
    370                 375                 380

Ile Val Leu Leu Ile Lys Arg Ser Arg
385                 390
```

```
<210> SEQ ID NO 44
<211> LENGTH: 395
<212> TYPE: PRT
<213> ORGANISM: Streptococcus agalactiae

<400> SEQUENCE: 44
```

| | | | | | | | | | | | | | | |
|---|---|---|---|---|---|---|---|---|---|---|---|---|---|---|
| Met | Pro | Lys | Leu | Ile | Val | Ser | Phe | Leu | Cys | Ile | Leu | Leu | Ser | Leu | Thr |
| 1 | | | | 5 | | | | | 10 | | | | | 15 | |
| Cys | Val | Asn | Ser | Val | Gln | Ala | Glu | Glu | His | Lys | Asp | Ile | Met | Gln | Ile |
| | | | 20 | | | | | 25 | | | | | 30 | | |
| Thr | Arg | Glu | Ala | Gly | Tyr | Asp | Val | Lys | Asp | Ile | Asn | Lys | Pro | Lys | Ala |
| | | 35 | | | | | 40 | | | | | 45 | | | |
| Ser | Ile | Val | Ile | Asp | Asn | Lys | Gly | His | Ile | Leu | Trp | Glu | Asp | Asn | Ala |
| 50 | | | | | 55 | | | | | 60 | | | | | |
| Asp | Leu | Glu | Arg | Asp | Pro | Ala | Ser | Met | Ser | Lys | Met | Phe | Thr | Leu | Tyr |
| 65 | | | | | 70 | | | | | 75 | | | | | 80 |
| Leu | Leu | Phe | Glu | Asp | Leu | Ala | Lys | Gly | Lys | Thr | Ser | Leu | Asn | Thr | Thr |
| | | | | 85 | | | | | 90 | | | | | 95 | |
| Val | Thr | Ala | Thr | Glu | Thr | Asp | Gln | Ala | Ile | Ser | Lys | Ile | Tyr | Glu | Ile |
| | | | 100 | | | | | 105 | | | | | 110 | | |
| Ser | Asn | Asn | Asn | Ile | His | Ala | Gly | Val | Ala | Tyr | Pro | Ile | Arg | Glu | Leu |
| | | 115 | | | | | 120 | | | | | 125 | | | |
| Ile | Thr | Met | Thr | Ala | Val | Pro | Ser | Ser | Asn | Val | Ala | Thr | Ile | Met | Ile |
| 130 | | | | | 135 | | | | | 140 | | | | | |
| Ala | Asn | His | Leu | Ser | Gln | Asn | Asn | Pro | Asp | Ala | Phe | Ile | Lys | Arg | Ile |
| 145 | | | | | 150 | | | | | 155 | | | | | 160 |
| Asn | Glu | Thr | Ala | Lys | Lys | Leu | Asp | Met | Thr | Lys | Thr | His | Phe | Tyr | Asn |
| | | | | 165 | | | | | 170 | | | | | 175 | |
| Pro | Ser | Gly | Ala | Val | Ala | Ser | Ala | Phe | Asn | Gly | Leu | Tyr | Ser | Pro | Lys |
| | | | 180 | | | | | 185 | | | | | 190 | | |
| Glu | Tyr | Asp | Asn | Asn | Ala | Thr | Asn | Val | Thr | Thr | Ala | Arg | Asp | Leu | Ser |
| | | 195 | | | | | 200 | | | | | 205 | | | |
| Ile | Leu | Thr | Tyr | His | Phe | Leu | Lys | Lys | Tyr | Pro | Asp | Ile | Leu | Asn | Tyr |
| 210 | | | | | 215 | | | | | 220 | | | | | |
| Thr | Lys | Tyr | Pro | Glu | Val | Lys | Ala | Met | Val | Gly | Thr | Pro | Tyr | Glu | Glu |
| 225 | | | | | 230 | | | | | 235 | | | | | 240 |
| Thr | Phe | Thr | Thr | Tyr | Asn | Tyr | Ser | Thr | Pro | Gly | Ala | Lys | Phe | Gly | Leu |
| | | | | 245 | | | | | 250 | | | | | 255 | |
| Glu | Gly | Val | Asp | Gly | Leu | Lys | Thr | Gly | Ser | Ser | Pro | Ser | Ala | Ala | Phe |
| | | | 260 | | | | | 265 | | | | | 270 | | |
| Asn | Ala | Leu | Val | Thr | Ala | Lys | Arg | Gln | Asn | Thr | Arg | Leu | Ile | Thr | Val |
| | | 275 | | | | | 280 | | | | | 285 | | | |
| Ile | Leu | Gly | Val | Gly | Asp | Trp | Ser | Asp | Gln | Asp | Gly | Glu | Tyr | Tyr | Arg |
| 290 | | | | | 295 | | | | | 300 | | | | | |
| His | Pro | Phe | Val | Asn | Ala | Leu | Val | Glu | Lys | Gly | Phe | Lys | Asp | Ala | Lys |
| 305 | | | | | 310 | | | | | 315 | | | | | 320 |
| Asn | Ile | Ser | Ser | Lys | Thr | Pro | Val | Leu | Lys | Ala | Val | Lys | Pro | Lys | Lys |
| | | | | 325 | | | | | 330 | | | | | 335 | |
| Glu | Val | Thr | Lys | Thr | Lys | Thr | Lys | Ser | Ile | Gln | Glu | Gln | Pro | Gln | Thr |
| | | | 340 | | | | | 345 | | | | | 350 | | |
| Lys | Glu | Gln | Trp | Trp | Thr | Lys | Thr | Asp | Gln | Phe | Ile | Gln | Ser | His | Phe |
| | | 355 | | | | | 360 | | | | | 365 | | | |
| Val | Ser | Ile | Leu | Ile | Val | Leu | Gly | Thr | Ile | Ala | Ile | Leu | Cys | Leu | Leu |
| 370 | | | | | 375 | | | | | 380 | | | | | |

Ala Gly Ile Val Leu Leu Ile Lys Arg Ser Arg
385                 390                 395

<210> SEQ ID NO 45
<211> LENGTH: 1771
<212> TYPE: DNA
<213> ORGANISM: Streptococcus agalactiae

<400> SEQUENCE: 45

| | | | | | |
|---|---|---|---|---|---|
| ataccatacc | gtttaatgag | attcataatt | cacaggttgc | tttagagcat | gaagcaaagg | 60 |
| tgtctaagat | ttctgaagag | caactgtact | acttgatgag | tcgaggttta | tctgaagctg | 120 |
| aggcaacaga | aatgattgtt | atggggtttg | ttgagcccct | tacgaaagaa | ttaccaatgg | 180 |
| aatatgcggt | agagttaaac | cgcttaattt | cctatgaaat | ggaaggttca | gttggttaat | 240 |
| tgaagatttc | aagagataat | aaaaagcccc | tatgttattg | atgaaggggg | cttttatatt | 300 |
| agcacagtta | ttatctagag | cgctttataa | gtaatactat | cccagctaaa | agacaaagga | 360 |
| tagcgatggt | gcccagaaca | attaaaatag | atacaaaatg | tgattgaata | aattgatctg | 420 |
| ttttttgtcca | ccactgttct | tttgtttgag | gctgttcttg | aatagatttg | gttttggttt | 480 |
| tagtaacttc | ttttttaggt | ttaacggctt | taatacagg | agttttagaa | gaaatatttt | 540 |
| tagcgtctttt | aaaaccttttt | tctacaagag | cgttgacaaa | cggatgacga | tagtactctc | 600 |
| cgtcttggtc | tgaccaatca | ccaactccta | aaaccacagt | tatcaagcga | gtattctggc | 660 |
| gtttagctgt | aactaaggca | ttaaaagcag | cgctagggct | agaaccagtt | tttaagccat | 720 |
| ctactccttc | taatccaaat | ttagcgccgg | gggtagagta | gttataagtt | gtaaatgttt | 780 |
| cttcataagg | agttccgacc | atggccttga | cttcaggata | ttttgtatag | ttcagtatat | 840 |
| cagggtattt | tttaaggaaa | tgataggtta | aaattgatag | atcacgtgca | gtcgtaacgt | 900 |
| tagtagcatt | gttatcgtat | tcttttgggg | agtaaagtcc | attaaaagca | ctcgctaccg | 960 |
| ccccactggg | gttataaaag | tgagttttttg | tcataccgag | tttcttggcg | gtttcattga | 1020 |
| ttcgtttaat | gaaggcgtca | ggattgtttt | gtgataagtg | gttagcaatc | ataatagttg | 1080 |
| ctacattaga | tgacgggaca | gctgtcatag | taatcagttc | acgaatagga | taagcaaccc | 1140 |
| cagcatgaat | attattatta | ctaatttcat | aaatcttact | tatggcttgg | tctgtttctg | 1200 |
| ttgcagtcac | tgtggtgttg | aggcttgttt | ttccttttagc | taagtcttca | aatagtaaat | 1260 |
| ataaagtaaa | cattttttagac | atgctagcgg | gatcacgttc | taaatcagcg | ttatcttccc | 1320 |
| acaaaatatg | acctttattg | tcaataacga | tagacgcttt | aggtttatta | atatctttaa | 1380 |
| catcatatcc | ggcttctcgg | gtaatttgca | taatatcttt | atgttcttca | gcttgcacag | 1440 |
| agtttacaca | agtcagggat | aataaaatgc | agaggaaaga | tacgattaat | ttaggcatag | 1500 |
| gtaactcctg | aaaactttttt | attaatatta | taacaaaaaa | tcactaataa | aaaagacatt | 1560 |
| tcattagtga | ttttttaattt | tatatattct | cctaaaccta | gctaaagaaa | ctgctgtgca | 1620 |
| gcaactcctt | gtgtcaaagg | gagattacta | ttaaagttttt | tcgttaacgt | agcgcacaaa | 1680 |
| atgattccac | cacactttga | ggaagaaact | gcgctcaata | ctatcttttg | ccactaaatg | 1740 |
| aacgctaggt | tcctttatga | gatagccttt | t | | | 1771 |

<210> SEQ ID NO 46
<211> LENGTH: 1188
<212> TYPE: DNA
<213> ORGANISM: Streptococcus agalactiae

<400> SEQUENCE: 46
atgcctaaat taatcgtatc tttcctctgc attttattat ccctgacttg tgtaaactct     60

```
gtgcaagctg aagaacataa agatattatg caaattaccc gagaagccgg atatgatgtt    120
aaagatatta ataaacctaa agcgtctatc gttattgaca ataaaggtca tattttgtgg    180
gaagataacg ctgatttaga acgtgatccc gctagcatgt ctaaaatgtt tactttatat    240
ttactatttg aagacttagc taaaggaaaa acaagcctca acaccacagt gactgcaaca    300
gaaacagacc aagccataag taagatttat gaaattagta ataacaatat tcatgctggg    360
gttgcttatc ctattcgtga actgattact atgacggctg tcccgtcatc taatgtagca    420
actattatga ttgctaacca cttatcacaa aacaatcctg acgccttcat taaacgaatc    480
aatgaaaccg ccaagaaact cgatatgaca aaaactcact tttataaccc tagtggggcg    540
gtagcaagtg cttttaatgg actttactcc ccaaaagaat acgataacaa tgctactaac    600
gttacgactg cacgtgatct atcaatttta acctatcatt tccttaaaaa atacctgat     660
atactgaact atacaaaata tcctgaagtc aaggccatgg tcggaactcc ttatgaagaa    720
acatttacaa cttataacta ctctaccccc ggcgctaaat ttggattaga aggagtagat    780
ggcttaaaaa ctggttctag ccctagcgct gcttttaatg ccttagttac agctaaacgc    840
cagaatactc gtttgataac tgtgatttta ggcgttggcg attggtcaga ccaagacgga    900
gagtactatc gtcatccgtt tgtcaacgct cttgtagaaa aaggttttaa agacgctaaa    960
aatatttctt ctaaaactcc tgtattaaaa gccgttaaac ctaaaaaaga agttactaaa   1020
accaaaacca aatctattca agaacagcct caaacaaaag aacagtggtg gacaaaaaca   1080
gatcaattta ttcaatcaca ttttgtatct attttaattg ttctgggaac catcgctatc   1140
ctttgtcttt tagctgggat agtattactt ataaagcgct ctagataa               1188
```

DETECTION OF PENICILLIN TOLERANCE IN GROUP B STREPTOCOCCUS: SINGLE NUCLEOTIDE POLYMORPHISMS IN PENICILLIN BINDING PROTEIN 4

CROSS-REFERENCE TO RELATED APPLICATIONS

The present application claims the benefit of priority under 35 U.S.C. §119(e) to U.S. Provisional Application No. 61/127,891 filed May 16, 2008, and 61/190,481 filed Aug. 29, 2008, the entire disclosures of which are hereby incorporated by reference in their entirety.

FIELD

Example embodiments are generally directed to a highly specific detection assay for penicillin tolerance in Group B Streptococcus. More specifically, the present invention relates to the detection of at least one single nucleotide polymorphism in penicillin binding protein 4, which is indicative of penicillin tolerance in Group B Streptococcus.

BACKGROUND

Group B Streptococcus (GBS) afflicts about 8,000 newborns and 18,000 people in the United States annually. It represents the most common cause of blood infections and meningitis in newborns and is a frequent cause of newborn pneumonia. It is one of the leading causes in neonatal infections. Under the Centers for Disease Control (CDC) guidelines, pregnant women are screened for GBS at 35-37 weeks of gestation. Women positive for GBS are treated with β-lactam antibiotics, such as penicillin, four hours prior to delivery (Gibbs et al., 2004; Schrag et al., 2002).

In addition to pregnant women and infants, GBS also afflicts others, such as the elderly and those having underlying conditions such as diabetes or a compromised immune defense (Sendi et al., 2008).

Penicillin treatment appears effective in most incidents for GBS, and no cases of penicillin resistance have been reported. However, despite the penicillin treatment, GBS is occasionally found as evidenced by positive culture assay. This is attributed to penicillin tolerance (PT). GBS, when penicillin tolerant, exhibits growth inhibition during the penicillin treatment; but escapes to become viable when penicillin is taken off the treatment regimen. Using a culture and plating system to measure viability, Betriu et al. (1994) has reported that ~17% of the clinical isolates demonstrate PT phenotype. Little is known about this PT phenotype behavior in GBS, let alone its underlying mechanisms. Currently, there is no screening test for PT in GBS, thus useful information is unavailable to improve current penicillin treatment (such as prolonging administration of penicillin).

The bactericidal action of penicillin occurs in two steps. The first step is the inhibition of growth via the binding of penicillin to the penicillin binding proteins (PBPs). The second step is the cidal step in which bacterial lytic enzymes are upregulated and secreted which subsequently disrupts the membrane potential and triggers autolysis. At least seven (7) PBPs have been found on the cell wall of bacteria and they share co-ordinate activities in cell wall synthesis. Different PBPs possess different biological properties. For example, PBP1a, 1b, 2a, and 2b contain structural domains essential in sugar synthesis and peptide linkage, whereas PBP4 is a D-alanyl-D-alanine carboxypeptidase (Macheboeuf et al., 2006).

It has been hypothesized that PT is a result of disconnection between the first step and the second step. Accordingly, PT converts penicillin from a bactericidal drug to a bacterial static drug. In other bacterial species such as Staphylococcus aureus and Streptococcus pneumoniae, it is suggested that PT in these species may be related to alterations in gene expression; more particularly, increased expression of lrgAB or lytSR may result in a penicillin tolerance phenotype (Rice and Bayles, 2008). Accordingly, there is a continuing need to provide a specific screening test for penicillin tolerance in Group B Streptococcus in mammals.

SUMMARY

The present inventors discovered two novel single nucleotide polymorphisms (SNPs) in penicillin binding protein 4 (PBP4) and that the presence of one or both of two SNPs in PBP4 is a highly specific marker for PT in GBS.

Accordingly, methods are provided for detecting penicillin tolerance in Group B Streptococcus. The methods include detecting at least one of two novel SNPs in penicillin binding protein 4, as the presence of one or both SNPs is indicative of penicillin tolerance in GBS. More specifically, the methods include the steps of: (a) providing a biological sample and (b) detecting at least one single nucleotide polymorphism in the biological sample, where at least one SNP is G503A and/or G865A, and wherein the presence of at least one of these SNPs is indicative of a penicillin tolerance in Group B Streptococcus The biological sample may be any suitable sample from a mammal, including, but not limited to, a cervicovaginal swab, a rectal swab, whole blood, urine, cerebrospinal fluid, ascites fluid, and the like.

The detecting steps may be performed by a PCR technology selected from the group consisting of real-time PCR, pyrosequencing, conventional PCR followed by sequencing and the like.

According to non-limiting example embodiments, the detecting step may be performed by a real-time polymerase chain reaction (PCR). Such real-time PCR methods may include for example, the use of molecular beacon, TaqMan, FRET, or LNA probe technology. Detecting may also include pyrosequencing in addition to real-time PCR.

Further provided are methods of determination of said nucleic acid originates from Group B Streptococcus. According to example embodiments, the primer set may be specific for both or at least one of the SNPs and for GBS. Alternatively, at least two primer sets may be used; where one primer set is specific for at least one SNP, another primer set is specific for GBS. The detection of a single nucleotide polymorphism (SNP) and of GBS may be substantially simultaneously or it may be at different times (i.e., sequentially). The determination may relate to the use of primer sets against a GBS-species specific gene (e.g., cfb CAMP factor gene; Christie, Atkins, and Munch-Petersen, 1944).

According to other non-limiting example embodiments, the detecting step may be performed by conventional PCR followed by sequencing.

Also provided are isolated oligonucleotides having a nucleotide sequence selected from the group consisting of SEQ ID NO: 1, SEQ ID NO: 2, SEQ ID NO: 3 and SEQ ID NO: 4 and sequences having a 95% or greater identity with such sequences.

Also provided are isolated oligonucleotides having a nucleotide sequence selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12; as well as sequences having a 95% or greater identity with such sequences. Further provided are isolated oligonucleotides having a nucleotide sequence selected from the group consisting of SEQ ID NO: 17, SEQ ID NO: 18, and sequences having a 95% or greater identity with such sequences.

Isolated hybridization probes are also provided herein, including those selected from the group consisting of SEQ ID NO: 13, SEQ ID NO: 14, SEQ ID NO: 15, SEQ ID NO: 16, and SEQ ID NO: 19.

Further provided are methods of diagnosing penicillin tolerance that include testing a mammal for penicillin tolerance in Group B *Streptococcus* by a method that includes detecting at least one SNP in penicillin binding protein 4 in a biological sample from the mammal, and the SNP is selected from G503A and G865A, where the presence of at least one of the SNPs is indicative of penicillin tolerance in GBS. According to example embodiments, the mammal may be a pregnant mammal, such as a pregnant female human. According to other example embodiments, the mammal may be an elderly human or a human having a chronic condition such as diabetes or a compromised immune defense.

In yet another aspect, kits are provided for identifying penicillin tolerance in Group B *Streptococcus*. Example kits may include at least one primer set containing a forward primer and a reverse primer that are capable of being used to detect at least one SNP in penicillin binding protein 4 in a biological sample, selected from the group consisting of G503A and G865A, and instructions to use the primer set to detect the at least one SNP, where the presence of at least one SNP in penicillin binding protein 4 may be indicative of penicillin tolerance in GBS. Example embodiments may also include at least one hybridization probe, and the instructions may include instructions for using the forward primer and reverse primer in performing real-time PCR in detecting penicillin tolerance in a biological sample.

Example kits may include at least one primer set containing at least one forward primer and at least one reverse primer, wherein the forward primer is selected from the group consisting of nucleotide sequence SEQ ID NO:5, SEQ ID NO: 6, SEQ ID NO: 7, SEQ ID NO: 8, and SEQ ID NO: 17, and the reverse primer is selected from the group consisting of SEQ ID NO: 9, SEQ ID NO:10, SEQ ID NO:11, SEQ ID NO:12, and SEQ ID NO: 18; and (b) instructions for using said forward primer and reverse primer to detect penicillin tolerance in Group B *Streptococcus* in a biological sample.

Example kits also include at least one primer set containing at least one forward primer and at least one reverse primer, wherein the forward primer is selected from the group consisting of nucleotide sequence SEQ ID NO: 1 and SEQ ID NO: 2, and the reverse primer selected from the group consisting of nucleotide sequence SEQ ID NO: 3 and SEQ ID NO: 4; and (b) an instructions for using the forward and reverse primers to detect penicillin tolerance in GBS. The instructions may include instructions for detecting at least one SNP in PBP4 in a biological sample selected from G503A and G865A. Exemplary primer pairs include SEQ ID NOs: 1 and 3, as well as SEQ ID NOs: 2 and 4.

BRIEF DESCRIPTION OF THE FIGURES

Embodiments of the invention are herein described, by way of non-limiting example, with reference to the following accompanying Figures.

FIG. 1 depicts the results of a microbroth penicillin tolerance assay on different GBS laboratory strains.

FIG. 2 depicts penicillin tolerant GBS strains that withstand penicillin induced lysis.

FIG. 3 depicts penicillin tolerance and cell viability measured by intracellular ATP concentration.

FIG. 4 depicts penicillin tolerance assay by Propidium Iodide cell viability staining and FACS analysis.

FIG. 5 depicts BLASTP analysis of penicillin binding protein 4, comparing susceptible and penicillin tolerant GBS strains.

FIG. 6 depicts the A909 (susceptible GBS strain) genome sequence (165921 to 167691 bp) and the primers used to PCR amplify and sequence identify the SNPs G503A (G168D amino acid polymorphism) and G865A (V289I amino acid polymorphism). The PBP4 gene is depicted as the reverse complement within the genome sequence. AP1 and AP2 represent the forward and reverse primers for SNP G503A (G168D amino acid polymorphism). AP4 and AP3 represent the forward and reverse primers for SNP G865A (V289I amino acid polymorphism).

FIG. 7 depicts the NEM316 (penicillin tolerant GBS strain) gene sequence for penicillin binding protein 4 (PBP4), containing primers and probes that may be used in accordance with the present methods to detect at least one SNP and thus determine penicillin tolerance in GBS.

FIG. 8 depicts the effects of pbp4 allele replacement in A909 and O90R on membrane permeability and cell viability.

FIG. 9 depicts the effects of pbp4 replacement in A909 and O90R on cell viability.

FIG. 10 depicts differences in the peptidoglycan structural integrity between S and PT strains. Peptidoglycan layers of GBS strains at early-exponential phase were isolated and digested with lysozyme and mutanolysin. Peptidoglycan muropeptides were then separated by SDS-PAGE.

DETAILED DESCRIPTION

The aspects, advantages and/or other features of example embodiments of the invention will become apparent in view of the following detailed description, taken in conjunction with the accompanying drawings. It should be apparent to those skilled in the art that the described embodiments of the present invention provided herein are merely exemplary and illustrative and not limiting. Numerous embodiments of modifications thereof are contemplated as falling within the scope of the present invention and equivalents thereto. All publications, patent applications, patents, and other references mentioned herein are incorporated by reference in their entirety.

In describing example embodiments, specific terminology is employed for the sake of clarity. However, the embodiments are not intended to be limited to this specific terminology.

As used herein, "a" or "an" may mean one or more. As used herein, "another" may mean at least a second or more.

As used herein, the term "biological sample" is used in its broadest sense. Example "samples" may include but is not limited to, fluid or tissue samples such as cervicovaginal swab, rectal swab, whole blood, urine, cerebrospinal fluid and ascites fluid and the like from a mammal such as a human or domestic animal. Methods of extraction of nucleic acids from biological samples are known to those of skill in the art.

As used herein, an "isolated" oligonucleotide refers to an oligonucleotide that is synthesized chemically (not a naturally occurring nucleic acid).

The term "nucleic acid" refers to covalently linked sequences of nucleotides in which the 3' position of the pentose of one nucleotide is joined by a phosphodiester group to the 5' position of the pentose of the next, and in which the nucleotide resides (bases) are linked in specific sequence.

The term "primer" refers to an oligonucleotide used in a polymerase chain reaction (PCR) reaction. The term "oligonucleotide" refers to a short polynucleotide, such as a polynucleotide having approximately 16-30 nucleotides.

The term "probe" is used interchangeably with the term "hybridization probe" and is used in the detection of SNP in real-time PCR.

The term "purified" refers to the result of a process that removes at least some (but not necessarily all) contaminants from the component of interest, such as a protein or nucleic acid.

The term "single nucleotide polymorphism" (or SNP) is a variation from the most frequently occurring base at a particular nucleic acid position.

The present inventors have established a highly specific correlation for particular SNP genotypes in penicillin binding protein 4 and the presence of a phenotypic trait (i.e., penicillin tolerance against Group B *Streptococcus* in mammals). The high specificity of this SNP correlation with penicillin tolerance provides a reliable and specific prediction that the presence of a specific SNP is a good predictor for occurrence of penicillin tolerance against Group B *Streptococcus*. Accordingly, the present invention provides, inter alia, useful tools for physicians to make proper diagnosis and treatment regimens that would lower the incidence or eliminate the risks of Group B *Streptococcus*, e.g., in neonatal care. SNP genotyping of an individual (such as a pregnant woman or an elderly person) enables doctors to select an appropriate medication, dosage regimes, and duration of treatment that will be effective based on an individual's SNP genotype.

In particular, the present inventors have discovered two amino acid polymorphisms present on penicillin binding protein 4 of Group B *Streptococcus* that are highly specific and bear a high correlation with the phenotype of penicillin tolerance for Group B *Streptococcus*.

The first single amino acid polymorphism identified by the present inventors is G168D. In this polymorphism, a G nucleotide at the 503 position has mutated into A. This is due to the G503A single nucleotide polymorphism of the penicillin binding protein 4 gene. Normally, the nucleotide sequence (i.e., GGT) encodes the amino acid glycine. Because of the SNP, however, the nucleotide mutates into GAT and encodes aspartic acid.

The second single amino acid polymorphism identified by the present inventors is V289I. In this amino acid polymorphism, the G nucleotide at the 865 position has mutated into A. This is due to the G865A single nucleotide polymorphism of the penicillin binding protein 4 gene. Normally, the nucleotide sequence (i.e., GTT) encodes the amino acid valine. Because of the SNP, the nucleotide mutates into ATT and encodes isoleucine.

The present inventors further discovered that these two amino acid polymorphisms (G168D and V289I) are concomitantly present on penicillin binding protein 4 of penicillin tolerant GBS strains. Using conventional PCR assays, we tested 57 GBS strains, of which 13 exhibit at least one SNP and were penicillin tolerant. In these 13 tolerant GBS strains, we have identified the simultaneous presence of these two amino acid polymorphisms (i.e., when G168D is present, V289I is also present and vice versa) (Table 11). So far, we observation no single amino acid polymorphism presence without another (i.e. when G168D is present, V289I is absent and vice versa). Accordingly, these two amino acid polymorphisms appear to be in absolute linkage disequilibrium. Without wishing to be bound by any theory it believed that these polymorphisms may represent a GBS subgroup or clade, supported by the fact that all GBS strains with these two SNPs are found within the Ia or non-typeable serotypes (Table 12).

It is to be understood that the detection of one of these two amino acid polymorphisms is a reliable predictor of penicillin tolerance (either G168D or V289I). In one embodiment, detection may be performed by real-time PCR to detect either SNP (i.e., either G503A or G865A). In another embodiment, detection may be performed by conventional PCR followed by sequencing to detect either SNP. In a further embodiment, detection may be performed by real-time PCR to detect one SNP while a conventional PCR may be used to detect the other SNP (either G503A or G865A).

Provided herein are methods of detecting penicillin tolerance for Group B *Streptococcus*. The methods include detecting novel single nucleotide polymorphisms (SNPs) in penicillin binding protein 4 of a biological sample, as the presence of one or both SNPs is indicative of penicillin tolerance in GBS. More specifically, the methods include the steps of: (a) providing a biological sample and (b) detecting at least one single nucleotide polymorphism (SNP) in penicillin binding protein 4 in the biological sample, where the at least one SNP is G503A and/or G865A, and wherein the presence of at least one of these SNPs is indicative of a penicillin tolerance in Group B *Streptococcus*.

Providing a biological sample may include for example, collecting a sample from a mammal, and isolating nucleic acids (e.g., genomic) from cells of the sample. The biological sample collected from the mammal may be any suitable biological sample as would be apparent to those skilled in the art, and may include for example, a cervicovaginal swab, a rectal swab, whole blood, urine, cerebrospinal fluid, ascites fluid, and the like.

It is understood that there are many methodologies currently existing for the detection of single nucleotide polymorphisms (SNPs) that are present in genomic DNA. SNPs are DNA point mutations or insertions/deletions that are present at measurable frequencies in the population. SNPs are the most common variations in the genome. SNPs occur at defined positions within genomes and can be used for gene mapping, defining population structure, and performing functional studies. Sometimes, SNPs are useful as markers because many known genetic diseases are caused by point mutations and insertions/deletions. As indicated above, the present inventors have discovered SNPs in penicillin binding protein 4, which serve as a highly specific marker for penicillin tolerance in Group B *Streptococcus*. In particular, as indicated above, nucleotide SNPs G503A and/or G865A are highly indicative of penicillin tolerance in GBS. Accordingly, the present methods provide for the detection of one or both of these particular SNPs.

According to non-limiting example embodiments, detection may occur by contacting the nucleic acid sample with one or more primers that specifically hybridize to a region of the isolated nucleic acid containing a target SNP under conditions such that hybridization and amplification of the gene occurs, and determining the nucleotide presence at the SNP position, or in some instances, detecting the presence or absence of an amplification product.

It is contemplated that detection of SNPs in penicillin binding protein 4 can be performed in a variety of ways. For example, as indicated above, a variety of technologies related to real-time polymerase chain reaction (PCR) have been adapted to perform SNP detection. According to non-limiting example embodiments, the detecting step may be performed by real-time PCR.

In example embodiments, SNP detection using real-time amplification may be used. Optimal real-time PCR is provided to detect SNPs in penicillin binding protein 4. In example embodiments an analytical detection, such as a fluorescence detection method may be provided, in conjunction with PCR based on specific primers directed at SNP regions within the penicillin binding protein 4. In such embodiments, SNP detection using real-time amplification relies on the ability to detect amplified segments of nucleic acid as they are during the amplification reaction.

Presently, three basic real-time SNP detection methodologies exist: (i) increased fluorescence of double strand DNA specific dye binding, (ii) decreased quenching of fluorescence during amplification, and (iii) increased fluorescence energy transfer during amplification. All these techniques are non-gel based and each detection methodology may be conveniently optimized to detect SNPs in penicillin binding protein 4.

According to non-limiting example embodiments, real-time PCR may be performed using exonuclease primers (TaqMan® probes). In such embodiments, the exonuclease primers utilize the 5' exonuclease activity of thermostable polymerases such as Taq to cleave dual-labeled probes present in the amplification reaction (See, e.g., Wittwer, C. et al. *Biotechniques* 22:130-138, 1997). While complementary to the PCR product, the primer probes used in this assay are distinct from the PCR primer and are dually-labeled with both a molecule capable of fluorescence and a molecule capable of quenching fluorescence. When the probes are intact, intramolecular quenching of the fluorescent signal within the DNA probe leads to little signal. When the fluorescent molecule is liberated by the exonuclease activity of Taq during amplification, the quenching is greatly reduced leading to increased fluorescent signal. Non-limiting example fluorescent probes include 6-carboxy-floruescein moiety and the like. Exemplary quenchers include Black Hole Quencher 1 moiety and the like.

Detection of SNPs in penicillin binding protein 4 may be performed using real-time PCR, based on the use of intramolecular quenching of a fluorescent molecule by use of a tethered quenching moiety. Thus, according to example embodiments, real-time PCR methods may include the use of molecular beacon technology, using at least one primer set specific for at least one SNP in penicillin binding protein 4 selected from G503A and G865A. The molecular beacon technology utilizes hairpin-shaped molecules with an internally-quenched fluorophore whose fluorescence is restored by binding to a DNA target of interest (See, e.g., Kramer, R. et al. *Nat. Biotechnol.* 14:303-308, 1996). Increased binding of the molecular beacon probe to the accumulating PCR product can be used to specifically detect SNPs present in genomic DNA (i.e., penicillin binding protein 4

Methods provided herein may include the use any suitable primer set(s) capable of detecting SNP G503A in PBP4 and/or SNP G865A in PBP4. The selection of a suitable primer set may be determined by those skilled in the art, in view of this disclosure. By way of non-limiting example, the primers provided in Example 9, below may be used in detection of one or more SNPs.

Real-time PCR methods may also include the use of one or more hybridization probes, which may also be determined by those skilled in the art, in view of this disclosure. By way of non-limiting example, such hybridization probes may include one or more of those provided in Example 9, below, such as the HEX channel and/or FAM channel probes set forth therein.

According to example embodiments, probes and primers may be selected e.g., using an in silico analysis using primer design software and cross-referencing against the available nucleotide database of genes and genomes deposited at the National Center for Biotechnology Information (NCBI). Some additional guidelines may be used for selection of primers and/or probes. For example the primers and probes may be selected such that they are close together, but not overlapping. The primers may have the same (or close $T_M$) (e.g. between 58° C. and 60° C.). The $T_M$ of the probe may be approximately 10° C. higher than that selected for the $T_M$ of the primers. The length of the probes and primers should be between about 17 and 39 base pairs, etc. These and other guidelines may be useful to those skilled in the art in selecting appropriate primers and/or probes.

In these embodiments, real-time PCR may be performed using at least one primer set that includes a forward primer and a reverse primer. By way of non-limiting example, a primer set may be used that includes at least one forward primer selected from the group consisting of a nucleotide sequence consisting essentially of SEQ ID NO: 5, SEQ ID NO: 6, SEQ ID NO: 7, SEQ ID NO: 8, and SEQ ID NO: 17, and at least one reverse primer selected from the group consisting of a nucleotide sequence consisting essentially of SEQ ID NO: 9, SEQ ID NO: 10, SEQ ID NO: 11, SEQ ID NO: 12, and SEQ ID NO: 18. Nucleotide sequences "consisting essentially of" the listed sequences, include the sequences themselves as well as sequences having at least 95% sequence identity therewith.

Real-time PCR methods may also include the use of at least one isolated hybridization probe having a nucleotide sequence selected from the group consisting of SEQ ID NO: 13, SEQ ID NO: 14, SEQ ID NO: 15, and SEQ ID NO: 16. According to other embodiments, the real-time PCR methods may include the use of at least one isolated hybridization probe having a nucleotide sequence selected from the group consisting of SEQ ID NO: 13 and SEQ ID NO: 14, which represent the PBP4 penicillin tolerance (PT) forward and reverse complementary probes, respectively. According to yet other embodiments, the real-time PCR methods may include the use of at least one isolated hybridization probe having a nucleotide sequence selected from the group consisting of SEQ ID NO: 15 and SEQ ID NO: 16, which represent the PBP4 penicillin susceptible (S) forward and reverse complementary probes, respectively.

Real-time PCR reaction conditions may be selected based on the amplicon size, as well as the primer annealing temperatures. According to example embodiments, an anneal temperature may be in the range of about 56° C. to 64° C. Preferably, the anneal temperature is about 58° C. to 62° C. More preferably, the anneal temperature is 58° C. to 60° C. It should be understood, however, that an appropriate anneal temperature may vary based on various factors, such as the buffer used. For example, if a magnesium concentration of the buffer is varied, the anneal temperature may vary.

According to example embodiments, an anneal time may be in the range of about 15-70 seconds (preferably about 25-60 seconds, more preferably about 30 seconds), but may be varied as would be apparent to those skilled in the art, so long as annealing is achieved.

According to non-limiting example embodiments, teal-time PCR reactions may be performed e.g., using a Corbett Research Rotor-Gene RG-3000 (Corbett Research, Sydney, Australia) and include an initial incubation at 50° C. for 2 minutes followed by 95° C. for 2 minutes. Next, 45 cycles of denaturation (95° C., 20 s) and annealing/extension (60° C., 60 seconds) were performed with fluorescence acquisition (470 nM source/510 nM detection) immediately following each annealing/extension step. A final extension (72° C., 10 min) was performed.

Detecting may also include pyrosequencing in addition to real-time PCR. Pyrosequencing is a bioluminometric, non-electrophoretic technique that employs a cascade of coupled enzymatic reactions to monitor DNA synthesis. According to example embodiments, real-time PCR may be used to detect one or both SNPs as discussed herein, and pyrosequencing may be further used to ensure the quality and accuracy of the identification of SNPs. Pyrosequencing provides a sequencing analysis of about a 25 to 35 nucleotide fragment of target PCR amplicons.

Sequencing primers for pyrosequencing may be selected e.g., using pyrosequencing assay design software. According to non-limiting example embodiments, primers used for pyrosequencing in the present methods may include those described in Trama et al. "Detection of *Aspergillus fumigatus* and a Mutation that Confers Reduced Susceptibility to Itraconazole and Posaconazole by Real-Time PCR and Pyrosequencing," *J. Clinical Microbiology*, February 2005, p. 906-908.

Real-time PCR and pyrosequencing methods may be performed generally according to methods described e.g., in TRAMA et al., "Detection of *Aspergillus fumigatus* and a Mutation that Confers Reduced Susceptibility to Itraconazole and Posaconazole by Real-Time PCR and Pyrosequencing," *J. Clinical Microbiology*, February 2005, p. 906-908; TRAMA et al. "Detection and Identification of Candida species associated with *Candida vaginitis* by Real-Time PCR and Pyrosequencing." *Molecular and Cellular Probes* 19 (2005) 145-152; and ADELSON et al. "Simultaneous Detection of Herpes Simplex Virus Types 1 and 2 by Real-Time PCR and Pyrosequencing," *J. of Clinical Virology* 33 (2005) 25-34. Each of these references is incorporated herein by reference in their entireties.

By way of non-limiting example, pyrosequencing may be performed by the following method. For PCR product purification prior to pyrosequencing analysis, the bio-ITS3 primer may be synthesized with a 5' biotin modification, which is incorporated into the amplicon during the amplification process. The biotinylated PCR product is captured with streptavidin Sephadex, is then purified and denatured with a vacuum prep workstation according to the manufacturer's instructions (Biotage, Uppsala, Sweden). For the pyrosequencing reaction, 0.5 µM of each sequencing primer may be utilized to prime the biotinylated amplification products. A pyrosequencing 96 MA System (Biotage, Uppsala, Sweden) may be programmed with 10 cycles of an AGCT dispensation order. The resulting pyrosequencing data or programs being analyzed with PSQ 96 MA version 2.0.2 software. It should be understood that this method may be varied by those skilled in the art, without departing from the scope of the present disclosure.

According to other non-limiting example embodiments, the detecting step may be performed by conventional PCR followed by sequencing. In these embodiments, conventional PCR may be performed using at least one primer set that includes a forward primer and a reverse primer. For example, a primer set may be used that includes at least one forward primer having a nucleotide sequence consisting essentially of SEQ ID NO: 1 and at least one reverse primer having a nucleotide sequence consisting essentially of SEQ ID NO: 3. According to other non-limiting embodiments, conventional PCR may be performed using a primer set that includes at least one forward primer having a nucleotide sequence consisting essentially of SEQ ID NO: 2 and at least one reverse primer having a nucleotide sequence consisting essentially of SEQ ID NO: 4. Nucleotide sequences "consisting essentially of" the listed sequences, include the sequences themselves as well as sequences having at least 95% sequence identity therewith.

Conventional PCR conditions may be performed, for example, using a Biometra T3 Thermocycler. In particular, according to non-limiting example embodiments cycling conditions may include an initial denaturation step of 94° C. for 3 min. followed by 35 cycles of 94° C. for 1 min, 53° C. for 1 min. and 72° C. for 1 minute. A 10 minute extension step at 72° C. concludes each reaction.

Further provided are methods of determination of said nucleic acid originates from Group B *Streptococcus*. According to example embodiments, the primer set may be specific for both at least one of the SNPs and for GBS. Thus, example embodiments include methods that include PCR performed using at least one primer set, where the primer set is specific for at least one SNP in penicillin binding protein 4 selected from the group consisting of G503A and G865A, and is specific for Group B *Streptococcus*. Alternatively, at least two primer sets may be used, where one is specific for at least one SNP and at least one is specific for GBS. The detection of a SNP and of GBS may be substantially simultaneously or it may be at different times. Methods are provided that include detecting GBS using at least one primer set against a GBS-species specific gene (e.g., cJb CAMP factor gene), to determine for example that the presence of a SNP is in fact indicative of penicillin tolerance in GBS.

Further provided are methods of diagnosing penicillin tolerance that include testing a mammal for penicillin tolerance in Group B *Streptococcus* by a method that includes detecting at least one SNP in PBP4 in a biological sample from the mammal, selected from G503A and G865A, where the presence of at least one of the SNPs is indicative of penicillin tolerance in GBS. The presence of the SNP is indicative of penicillin tolerance in GBS. According to example embodiments, the mammal may be a pregnant female mammal, such as a pregnant female human. According to other example embodiments, the mammal may be an elderly human or a human having a chronic condition such as diabetes or a compromised immune defense, or other conditions that may result in the mammal being afflicted with GBS.

Methods provided herein may further include testing the mammal for Group B *Streptococcus*.

If the mammal is positive for penicillin tolerance, methods herein may further comprise administering a non-penicillin or a non-β-lactam antibiotic, such as erythromycin, clindamycin and the like to the mammal. In addition (or alternatively), if the mammal is positive for penicillin tolerance, the method further may include administering an antibiotic to the mammal for a longer time (e.g., >4 hours) than if the mammal is not penicillin tolerant.

Also provided are isolated oligonucleotide primers having a nucleotide sequence selected from the group consisting of SEQ ID NO: 1, SEQ ID NO: 2, SEQ ID NO: 3 and SEQ ID NO: 4 and sequences having a 95% or greater identity with such sequences.

Also provided are isolated oligonucleotide primers having a nucleotide sequence selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 17, and SEQ ID NO: 18 and sequences having a 95% or greater identity with such sequences.

Also provided are other isolated oligonucleotides from PBP4 that are capable of being used in PCR methods to determine the presence of SNP G503A and/or SNP G865A.

Further provided are isolated hybridization probes having a nucleotide sequence selected from the group consisting of SEQ ID NO: 13, SEQ ID NO: 14, SEQ ID NO: 15, SEQ ID NO: 16, and any other probes set forth herein. As would be apparent to those skilled in the art, other probes may be selected by those skilled in the art, such as probes that may be somewhat shorter or longer than those set forth herein, and still fall within the scope of the present invention.

According to example embodiments, the present invention provides kits that include at least one component to assist one in detecting penicillin tolerance in Group B *Streptococcus*.

By way of non-limiting example, kits may include at least one SNP detection reagent, such as a primer set (i.e., forward primers and reverse primers that target against amplification near the SNP regions of the penicillin binding protein 4). The sequences of the primer sets may be based for example on the SNPs provided in the Tables and/or Figures of the present disclosure and/or in the Sequence Listing.

For example, kits are provided for identifying penicillin tolerance in Group B *Streptococcus*. Example kits may include at least one primer set containing a forward primer and a reverse primer that are capable of being used to detect at least one single nucleotide polymorphism in Penicillin binding protein 4 in a biological sample, selected from the group consisting of G503A and G865A, and instructions to use the primer set to detect the at least one SNP. Such a kit may further include at least one hybridization probe. The instructions may include instructions for using the primers and/or a hybridization probe in performing real-time PCR in detecting penicillin tolerance in a biological sample.

Example kits may include at least one primer set containing at least one forward primer and at least one reverse primer, wherein the forward primer is selected from the group consisting of SEQ ID NO: 5, SEQ ID NO: 6, SEQ ID NO: 7, SEQ ID NO: 8, and SEQ ID NO: 17, and the reverse primer is selected from the group consisting of nucleotide sequence SEQ ID NO: 9, SEQ ID NO: 10, SEQ ID NO: 11, SEQ ID NO: 12, SEQ ID NO: 18; and (b) an instructions for using the forward and reverse primers to detect penicillin tolerance in GBS in a biological sample.

Example kits also include a primer set containing at least one forward primer and at least one reverse primer, wherein the forward primer is selected from the group consisting of nucleotide sequence SEQ ID NO: 1 and SEQ ID NO: 2, and the reverse primer is selected from the group consisting of nucleotide sequence SEQ ID NO: 3 and SEQ I)NO: 4; and (b) an instructions for using the forward and reverse primers to detect penicillin tolerance in GBS in a biological sample. The instructions may include instructions for detecting at least one SNP in PBP4 in a biological sample selected from G503A and G865A, using conventional PCR followed by sequencing. Example primer sets may include SEQ ID NO: 1 and SEQ ID NO: 3 or SEQ ID NO: 2 and SEQ ID NO: 4.

Various kits provided herein may include instructions for using the forward primer and reverse primer to detect specific SNPs and/or penicillin tolerance in GBS in a biological sample. The instructions present in such a kit may instruct the user for example, on how to use the components of the kit to perform the various methods provided herein. In particular, kits may include instructions for detecting SNPs using primer sets. The instructions may include for example, instructions for detecting at least one SNP in Penicillin binding protein 4, selected from G503A and G865A. These instructions can include a description of the detection methods, such as real-time PCR and detection by fluorescence spectroscopy. According to non-limiting example embodiments, instructions may include instructions for using a forward primer and a reverse primer in performing real-time PCR in detecting penicillin tolerance in a biological sample.

Example kits may also include at least one hybridization probe, such as hybridization probes that comprise fluorescent labels. In example methods using such a kit, either the released identifier nucleotide or the remaining probe may be determined using fluorescence spectroscopy, depending on the location of the fluorescent label within the probe. In example kits, the instructions may include instructions for using the forward primer and reverse primer in performing real-time PCR in detecting penicillin tolerance in a biological sample.

Further provided herein are kits that include a first primer set (such as those set forth in the embodiments discussed above), and a second primer set against a Group B *Streptococcus*-specific gene. Such kits may include instructions for using the first primer set to detect at least one SNP in PBP4 in a biological sample (e.g., where the SNP is from G503A and/or G865A), and for using the second primer set to determine if the presence of the SNP in PBP4 is indicative of penicillin tolerance in Group B *Streptococcus* in particular. According to non-limiting example embodiments, these examples may also include at least one hybridization probe and/or instructions for using the primer sets according to different detection methods, including for example those set forth herein.

Articles of manufacture and kits provided herein may additionally include reagents for carrying out the methods disclosed herein (e.g., buffers, Taq polymerase enzymes, cofactors, and agents to prevent contamination). Such reagents may be specific for one of the commercially available instruments described herein.

Further included in example kits, may be primers and/or probes that may be used in performing pyrosequencing.

The following examples are provided to further illustrate various non-limiting embodiments and techniques. It should be understood, however, that these examples are meant to be illustrative and do not limit the scope of the claims. As would be apparent to skilled artisans, many variations and modifications are intended to be encompassed within the spirit and scope of the invention.

EXPERIMENTAL EXAMPLES

Example 1

Minimum Bactericidal Concentration (MBC) and Minimum Inhibitory Concentration (MIC) Determination The inventors ascertained the incidence of antibiotic tolerance in GBS clinical isolates collected from cervicovaginal-rectal swabs, by investigating cell wall inhibitors used to eliminate GBS colonization in pregnant women before delivery as stated by the CDC guidelines. A ratio of the minimum bactericidal concentration (MBC) over minimum inhibitory concentration (MIC) after 24 h of antibiotic incubation or by determining quantitative kill curves has been used to define antibiotic tolerance previously.

The MBC:MIC ratio was calculated for laboratory strains using three β-lactam antibiotics (Penicillin G, Ampicillin, and Cefazolin) and a glycopeptide antibiotic (Vancomycin) (Table 1). Early-log phase cultures of GBS were treated with the individual antibiotics at a concentration of 0.25 to 512× $MIC_{90}$. The optical density ($OD_{600}$) of antibiotic treated cultures was used to determine the $MIC_{90}$ after 24 h and a cell count was used to determine their $MBC_{90}$. Susceptible, tolerant and intermediate strains were defined by their MBC: MIC ratio of $\leq 2:1$, $\geq 32:1$ and 4:1-16:1 respectively. Interestingly, the tolerant strains had a two-fold increase in their $MIC_{90}$ to the β-lactam antibiotics. The ratios characterized GBS strains A909 and 2603V/R as Susceptible, O90R as Tolerant, and NEM316 as Intermediate to Penicillin, Ampicillin, and Cefazolin. All four strains were susceptible to Vancomycin.

TABLE 1

$MBC_{90}:MIC_{90}$ Ratio Method of Determining Antibiotic Tolerance

| | | Penicillin G | Ampicillin | Cefazolin | Vancomycin |
|---|---|---|---|---|---|
| A909 | MBC (μg/ml) | 0.06 | 0.48 | 0.19 | 4 |
| | MIC (μg/ml) | 0.06 | 0.48 | 0.19 | 4 |
| | Ratio | 1 | 1 | 1 | 1 |
| | Phenotype | S | S | S | S |
| 2603V/R | MBC (μg/ml) | 0.06 | 0.48 | 0.39 | 4 |
| | MIC (μg/ml) | 0.06 | 0.48 | 0.19 | 4 |
| | Ratio | 1 | 1 | 2 | 1 |
| | Phenotype | S | S | S | S |
| NEM316 | MBC (μg/ml) | 0.48 | 1.92 | 3.12 | 4 |
| | MIC (μg/ml) | 0.06 | 0.48 | 0.19 | 4 |
| | Ratio | 8 | 4 | 16 | 1 |
| | Phenotype | I | I | I | S |
| O90R | MBC (μg/ml) | 3.84 | 15.36 | 12.5 | 4 |
| | MIC (μg/ml) | 0.12 | 0.96 | 0.39 | 4 |
| | Ratio | 32 | 32 | 32 | 1 |
| | Phenotype | PT | PT | PT | S |

Minimum Bactericidal Concentration (MBC), the minimum antibiotic concentration at which $\geq 90\%$ are non-viable cells, was determined by performing viability plate counts after 24 h antibiotic treatment. Minimum Inhibitory Concentration (MIC), the minimum concentration at which $\geq 90\%$ of cells are growth-inhibited, was determined by measuring $OD_{600}$ of an antibiotic treated well compared to untreated control. In bold is the 2-fold increase in $MIC_{90}$ of O90R (PT).

Example 2

Penicillin Tolerance Assay

A) GBS Laboratory Strains

An in vitro method involving microbroth (96-well) culture was used to develop a penicillin tolerance assay. In this assay, the inventors tested three laboratory bacterial strains (i.e., GBS strains A909, NEM316, and O90R). These cells were commercially obtained from ATCC source. Bacterial cells were cultured overnight for 18 hours at 37° C. in Todd-Hewitt Broth (THB). Subcultures in THB were subsequently grown to exponential phase ($OD_{600}$~0.3) at 37° C. Cell cultures were then exposed to different concentrations of penicillin G (Sigma, St. Louis, Mo.). The concentrations chosen were from 0.06 μg/mil to 15.4 μg/ml (which correspond to $1 \times MIC_{90}$ to $256 \times MIC_{90}$; MIC refers to minimal inhibition concentrations that inhibits 90% of cells) for a time duration of 48 hours at 37° C. Cell cultures were dispersed. A dilution (i.e., 1 to 20) of cells was re-plated into new wells containing fresh THB with 500 U Penase (to destroy residual penicillin). Cell cultures were allowed to grow for an additional 24 hours at 37° C. Assays were repeated four (4) times and standard bar represents standard deviations.

As shown in FIG. 1, after re-plate and culture for an additional 24-hours, laboratory strain A909 did not replicate, indicating penicillin effectively inhibits the replication or affects its viability. In contrast, penicillin did not inhibit the replication or viability of laboratory strain O90R, indicating that these cells are penicillin tolerant. Interestingly, laboratory strain NEM316 exhibits a phenomenon commonly known as "paradoxical effect." That is, after exposure to penicillin, these cells lose viability at the mid-range of penicillin concentrations (i.e., $16 \times MIC_{90}$ to $64 \times MIC_{90}$) (see FIG. 1) but exhibit viability at both low concentrations (i.e., $1 \times MIC_{90}$ to $8 \times MIC_{90}$) (see FIG. 1) and high concentrations (i.e., $128 \times MIC_{90}$ to $256 \times MIC_{90}$) (see FIG. 1).

The following definition of viability is used:

TABLE 2

| Viable growth | $OD_{600} \geq 0.1$ |
|---|---|
| Non-viable | $OD_{600} < 0.1$ |

The following definitions of phenotype are used:

TABLE 3

| Definition | Phenotype[1] |
|---|---|
| Susceptible | Growth $\leq 1 \times MIC_{90}$ |
| Intermediate | Growth $\geq 1 \times MIC_{90}$ to $\leq 16 \times MIC_{90}$ |
| Tolerant | Growth $\geq 1 \times MIC_{90}$ to $\leq 256 \times MIC_{90}$ |
| Paradoxical Effect | Growth $\geq 1 \times MIC_{90}$ to $\leq 8 \times MIC_{90}$ |
| | Inhibited Growth $\geq 16 \times MIC_{90}$ to $\leq 128 \times MIC_{90}$ |
| | Growth $\geq 32 \times MIC_{90}$ to $\leq 256 \times MIC_{90}$ |

[1]Phenotype: 48 hr penicillin treatment $MIC_{90}$; followed by 24 hr drug free culture.

Based on these phenotype definitions, the inventors characterized the three laboratory strains tested as follow:

TABLE 4

| GBS Laboratory Strains | Penicillin Phenotypes |
|---|---|
| A909 | Susceptible (S) |
| NEM316 | Paradoxical Effect-Penicillin Tolerance (PE-PT) |
| O90R | Penicillin Tolerance (PT) |

Thus, the inventors have established a microbroth assay to evaluate penicillin tolerant phenotypes in GBS and have shown that the strain O90R is penicillin tolerant.

B. GBS Clinical Isolate Strains

Using this established 96-well assay (i.e., microbroth assay), 115 clinical isolates of GBS were further tested. These were cervico-vaginal rectal clinical isolates (obtained from pregnant humans), and characterized their penicillin tolerance. The phenotype definitions (above) were used to identify the penicillin tolerant isolates. The results are summarized in Table 5.

TABLE 5

| % GBS Clinical Strains | Penicillin Phenotypes |
|---|---|
| 49% | Susceptible (S) |
| 8% | Intermediate |
| 27% | Paradoxical Effect-Penicillin Tolerance (PE-PT) |
| 16% | Penicillin Tolerance (PT) |

As shown in Table 5, as many as 16% of clinical strains tested so far is penicillin tolerant. This percentage appears to be similar to that reported by Betriu et al. (1994).

Example 3

Penicillin Tolerant GBS Strains Withstand Penicillin Induced Lysis

In this series of study, the three GBS laboratory strains (i.e., A909, NEM316, and O90R) were cultured for 18 hours at 37°

C. in THB. Subcultures in THB were subsequently grown to exponential phase ($OD_{600}$~0.3) at 37° C. Cells were treated with 100×$MIC_{90}$ Penicillin G for an additional 22 hours. $OD_{600}$ of these cell cultures before (O.D. initial) and after penicillin treatment (O.D. experimental) was measured (N=3). The values of O.D. experimental were subtracted from O.D. initial. (See FIG. 2).

As shown in FIG. 2, GBS strain A909 showed a decrease in OD, whereas GBS strains NEM316 and O90R did not. The difference is statistically significant (Student's t-test, paired; p=0.004). These data suggest that GBS penicillin tolerant strains do not undergo lysis upon penicillin treatment.

Example 4

Penicillin Tolerance and ATP Contents of GBS Strains

In an effort to further show the penicillin tolerance effect in GBS cells, the inventors measured the ATP contents in these cells after penicillin exposure. ATP is known to be a good indicator for cell viability, and poor level of ATP reveals low in cell viability. In this series of study, experiments were designed to monitor the changes in ATP contents in cells that were treated with penicillin.

GBS strains were cultured for 18 hours at 37° C. in THB. These cultures were used to inoculate fresh THB and subsequently allowed to grow to exponential phase ($OD_{600}$ 0.25-0.3) at 37° C. One (1) ml of culture was centrifuged at 5,000 g for 4 min. The cell pellet was re-suspended in ATP free water. Cellular ATP was extracted by using trichloroacetic acid (TCA) (5%) for 2 min. and subsequently neutralized with Tris-EDTA-0.1M NaOAc, pH 7.75 to 10×TCA volume. The initial (in.) cellular ATP concentration ([ATP]) was measured using the ENLITEN (Promega) luciferase based reaction kit. THB cultures then treated 100×$MIC_{90}$ Penicillin G for 22 hours. The experimental (exp.) cellular ATP was extracted and the concentration was measured as stated above. Based on the calculations ([ATP] exp.)/([ATP] in./O.D. in.), differences in viability were equated with the change in [ATP].

As shown in FIG. 3, GBS strain A909 showed a significant lesser [ATP] content as compared to those of NEM316 and O90R (See, FIG. 3). These data indicate that the penicillin tolerant strains maintain viability as shown by an elevated ATP cellular content. The ATP data is consistent with the microbroth assay (see, Example 2, FIG. 1). Accordingly, penicillin tolerant cells maintain cell viability despite exposure to penicillin and that they possess higher ATP levels.

Example 5

Penicillin Tolerance Assay—Evaluation of Clinical Isolates

In Example 2, penicillin tolerance assay using 96-well format was used. Although the assay is sensitive, an improved assay that accommodates a large volume size (i.e., 4 ml culture) (i.e., macrobroth penicillin tolerance assay), has been developed.

Using this modified penicillin tolerance assay, tolerant strains from the GBS clinical isolates can be more efficiently identified. In this macrobroth culture format, 25 ml THB broth GBS cultures (containing clinical isolates) were grown to an early exponential growth phase (~0.2 $OD_{600}$). Cell cultures (6 ml) were collected and divided into 4 culture tubes. Penicillin G (10×, 30×, 100×, and 300×$MIC_{90}$) were added to these cells and further incubated for 48 hours at 37° C. Cell cultures were shaken at 150 rpm in order to maintain cells in suspension for proper growth. Subcultures (1/20 dilution) of cells were put into fresh THB containing 250 U Penase (i.e., 100 µl of Penase 10,000 U stock into 4 ml THB culture). Subcultures were allowed to grow for 24 hours at 37° C. Cell growth was monitored by OD (see Example 2).

In the macrobroth assay, the criteria for phenotypes are based on the following definitions:

TABLE 6

| Definition | Phenotype |
| --- | --- |
| Susceptible | No Growth < 0.1 $OD_{600}$ |
| Penicillin Tolerance (PT) | Growth ≧ 0.1 $OD_{600}$ at 10 ×, 30, 100 ×, and 300 × $MIC_{90}$ |
| Paradoxical Effect PT | No growth < 0.1 $OD_{600}$ at 10 ×, 30, or 100 × $MIC_{90}$ and growth ≧ 0.1 $OD_{600}$ 300 × $MIC_{90}$ |

Based on these definitions, three phenotypes were identified with respect to the 51 clinical isolates and 6 laboratory strains tested:

TABLE 7

| GBS Laboratory Strains | Penicillin Phenotypes |
| --- | --- |
| A909, 2603V/R | Susceptible (S) |
| NEM316, COH1 | Paradoxical Effect-Penicillin Tolerance (PE-PT) |
| O90R, 515 | Penicillin Tolerance (PT) |

Table 8 summarizes the phenotype classification for the clinical GBS strains.

TABLE 8

| Clinical GBS Strain # (serotype) | Phenotype | 10×MIC | 30×MIC | 100×MIC | 300×MIC | Repeats |
| --- | --- | --- | --- | --- | --- | --- |
| 12 (III) | S | -- | -- | -- | -- | 2 |
| 18 (NT) | S | -- | -- | -- | -- | 2 |
| 21 (NT) | S | -- | -- | -- | -- | 2 |
| 26 (NT) | S | -- | -- | -- | -- | 2 |
| 46 (Ib) | S | -- | -- | -- | -- | 2 |
| 47 (III) | S | -- | -- | -- | -- | 2 |
| 71 (III) | S | -- | -- | -- | -- | 2 |
| 90 (Ib) | S | -- | -- | -- | -- | 2 |
| 91 (III) | S | -- | -- | -- | -- | 2 |
| 93 (Ib) | S | -- | -- | -- | -- | 2 |
| 101 (NT) | S | -- | -- | -- | -- | 2 |
| 122 (III) | S | -- | -- | -- | -- | 2 |
| 129 (V) | S | -- | -- | -- | -- | 2 |
| 131 (V) | S | -- | -- | -- | -- | 2 |
| 172 (NT) | S | -- | -- | -- | -- | 2 |
| 180 (V) | S | -- | -- | -- | -- | 2 |
| 193 (III) | S | -- | -- | -- | -- | 2 |
| 204 (V) | S | -- | -- | -- | -- | 2 |
| 211 (Ib) | S | -- | -- | -- | -- | 2 |
| 244 (Ib) | S | -- | -- | -- | -- | 2 |
| 272 (V) | S | -- | -- | -- | -- | 2 |
| 308 (V) | S | -- | -- | -- | -- | 2 |
| 316 (V) | S | -- | -- | -- | -- | 2 |
| 306 (II) | S | -- | -- | -- | -- | 2 |
| 307 (II) | S | -- | -- | -- | -- | 2 |
| 359 (V) | S | -- | -- | -- | -- | 2 |
| 367 (V) | S | -- | -- | -- | -- | 2 |
| 377 (V) | S | -- | -- | -- | -- | 2 |
| 378 (NT) | S | -- | -- | -- | -- | 2 |
| 379 (V) | S | -- | -- | -- | -- | 2 |
| 388 (NT) | S | -- | -- | -- | -- | 2 |
| A909 (Ia)* | S | -- | -- | -- | -- | 10> |

TABLE 8-continued

| Clinical GBS Strain # (serotype) | Phenotype | 10xMIC | 30xMIC | 100xMIC | 300xMIC | Re-peats |
|---|---|---|---|---|---|---|
| 2603V/R (V) | S | -- | -- | -- | -- | 5> |
| 68 (III) | PE-PT | + | -- | + | + | 2 |
| 97 (V) | PE-PT | -- | ++ | ++ | ++ | 2 |
| 264 (V) | PE-PT | +++ | ++ | -- | ++ | 2 |
| 268 (Ib) | PE-PT | ++ | -- | +++ | +++ | 2 |
| 273 (V) | PE-PT | -- | -- | -- | ++ | 2 |
| 311 (Ib) | PE-PT | -- | -- | + | + | 2 |
| 399 (V) | PE-PT | -- | + | + | + | 2 |
| COH1 (III) | PE-PT | -- | +++ | +++ | ++ | 2 |
| 127 (Ia) | PE-PT | -- | ++ | ++ | ++ | 2 |
| 156 (Ia) | PE-PT | -- | -- | -- | ++ | 2 |
| 296 (Ia) | PE-PT | -- | -- | ++ | -- | 2 |
| 357 (NT) | PE-PT | -- | -- | +++ | ++ | 2 |
| 380 (NT) | PE-PT | -- | -- | +++ | + | 2 |
| NEM316 (III) | PE-PT | +++ | -- | ++ | +++ | 10> |
| 22 (V) | PT | ++ | ++ | ++ | ++ | 2 |
| 279 (III) | PT | ++ | +++ | ++ | ++ | 2 |
| 320 (III) | PT | +++ | +++ | +++ | +++ | 2 |
| 60 (NT) | PT | + | ++ | + | + | 2 |
| 117 (Ia) | PT | + | + | + | + | 2 |
| 219 (Ia) | PT | + | + | + | + | 2 |
| 389 (Ia) | PT | ++ | +++ | +++ | +++ | 2 |
| 391 (NT) | PT | ++ | ++ | ++ | ++ | 2 |
| O90R (NT) | PT | +++ | +++ | +++ | +++ | 10> |
| 515 (Ia) | PT | ++ | +++ | ++ | ++ | 2 |

"--" indicates an O.D.$_{600}$ of 0.001 to 0.099
"+" indicates an O.D.$_{600}$ of 0.100 to 0.250
"++" indicates an O.D.$_{600}$ of 0.251 to 0.750
"+++" indicates an O.D.$_{600}$ of 0.751 to 1.500
*Bold face refers to laboratory strains As shown in Table 8 (above), out of the 51 clinical isolates tested, 31 clinical isolates can be classified as S (i.e., penicillin susceptible), eight (8) are PT (i.e., penicillin tolerant), and 12 are PE-PT (i.e., paradoxical effect—penicillin tolerant). Accordingly, out of the 51 clinical isolates, 60.8% are S, 15.7% are PT, and 23.5% are PE-PT. Notably, 15.7% of clinical isolates are found to be penicillin tolerant using the macrobroth assay (Table 7), which is similar to that of 16% using the microbroth assay (see above, Example 1). These data confirm that both the microbroth and the macrobroth assay can accurately identify penicillin tolerant phenotype in GBS cells.

In conclusion, using a culture system, the present inventors have identified at least three (3) phenotypes for GBS cells: susceptible, penicillin tolerant, and paradoxical effect-penicillin tolerance.

Example 6

Penicillin Tolerance Assay by Viability Staining and FACS Analysis

A viability staining assay was performed using Propidium Iodide (PI), a fluorescent molecule which is membrane permeable in non-viable cells. The proportion of live and dead cells within Penicillin treated cultures was measured. Cells were grown to early log phase followed by 100xMIC Penicillin treatment for 48 h and were stained with PI before measuring their fluorescence intensities by FACS. The results correlate with our macrobroth PKR assay data showing evidence of larger number of live cells in the PT population than in the S population, while the PE-PT population demonstrated an intermediate level of staining (FIG. 4).

Example 7

Identification of Amino Acid Polymorphisms in Penicillin Tolerant Strain—Role of Penicillin Binding Protein 4

After the inventors characterized the phenotypes for GBS, they further tested the possibility that penicillin tolerance may somehow relates to penicillin's effect on the multiple penicillin binding proteins (PBPs). The amino acid sequences among the different PBPs were compared; more specifically, the GBS Penicillin Binding Proteins 1a, 1b, 2a,2b, 2x, 3, 4, and 5 using BLASTP from NCBI (NIH). Five GBS genome sequenced strains (i.e., A909, 2603, COH1, NEM316, and 515) were used, looking for sequence differences that are unique to the COH1, NEM316, and 515 strains (which has been demonstrated to be the penicillin tolerant strains, see above) as compared to A909 and 2603V/R strains (which the inventors demonstrated to be penicillin susceptible strains).

GBS Penicillin Binding Proteins 1a, 1b, 2a, 2b, 2x, 3, and 5 did not show a penicillin tolerance specific polymorphism. In sharp contrast, the inventors identified two amino acid polymorphisms in PBP4 that are believed to be specific to penicillin tolerant strains (e.g., NEM316 and 515).

As shown in FIG. 5, the inventors observed polymorphisms at G168D (i.e., glycine to aspartic acid) and V289I (i.e., valine to isoleucine change) only in the penicillin tolerant strains (i.e., NEM316 and 515).

Two tolerance-specific amino acid polymorphisms, Gly168Asp and Val289Ile, were identified in highly conserved regions of the D-alanyl-D-alanine carboxypeptidase PBP4 from strains NEM316 (PE-PT) and 515 (PT). Upon investigating other PBP4 protein sequences from other bacterial species, only these tolerant GBS strains possess the non-conserved G168D amino acid polymorphism in PBP4, whereas the tolerant GBS, *Staphylococcus aureus*, and *Enterococcus faecalis* PBP4 possess the conserved V289I amino acid polymorphism.

Table 9 depicts PBP4 amino acid alignment from GBS and other bacterial species. The amino acid alignment shows two highly conserved regions of D-alanyl-D-alanine carboxypeptidase proteins from gram-positive and gram-negative species in which the G168D (Bold underlined amino acid) and V289I (Bold underlined amino acid) amino acid polymorphisms of GBS PBP4 were found.

TABLE 9

| ORGANISMS | D-ALANYL-D-ALANINE CARBOXYPEPTIDASE | |
|---|---|---|
| S. agalactiae 2603V/R & A909 | 163 TAKKLGMTKTHFYN 176 (SEQ ID NO: 24) | . . . 283 TRLITVVLGVGDW 295 (SEQ ID NO: 25) |

TABLE 9-continued

| ORGANISMS | D-ALANYL-D-ALANINE CARBOXYPEPTIDASE | |
|---|---|---|
| S. agalactiae NEM316 & O90R | 163 TAKKLDMTKTHFYN 176 (SEQ ID NO: 26) | . . . 283 TRLITVILGVGDW 295 (SEQ ID NO: 27) |
| Streptococcus pyogenes (MGAS6180) | 161 TAKQLGMTNTHFSN 174 (SEQ ID NO: 28) | . . . 281 TRLITIV**MGVGDW 293 (SEQ ID NO: 29) |
| Enterococcus faecalis (V583) | 177 KAAELGMTNTTYYN 190 (SEQ ID NO: 30) | . . . 297 FRLIEVILGVGNW 309 (SEQ ID NO: 31) |
| Staphylococcus aureus (N315) | 165 KAKAIGMKNTHFVN 178 (SEQ ID NO: 32) | . . . 279 FRINQVIMGAGDY 291 (SEQ ID NO: 33) |
| Streptomyces sp. K15 | 128 AATNLGLHNTHFDS 141 (SEQ ID NO: 34) | . . . 233 KTVIGTVLASTSI 245 (SEQ ID NO: 35) |
| Escherichia coli (strain K12) | 165 YVNALGLKNTHFQT 178 (SEQ ID NO: 36) | . . . 262 MRLISAVMGGRTF 274 (SEQ ID NO: 37) |
| Bacillus subtilis | 150 KAKELGLKNTSFKN 163 (SEQ ID NO: 38) | . . . 250 MRAIAVVFGASTP 262 (SEQ ID NO: 39) |
| Pseudomonas aeruginosa | 149 KAHALGMKNTRYVE 162 (SEQ ID NO: 40) | . . . 250 SPVNLVVLDAFGK 262 (SEQ ID NO: 41) |

Example 8

Sequence Identification of G168D and V289I Polymorphisms

The inventors examined if these two (2) amino acid polymorphisms may occur also in other penicillin tolerant strains. As described above, the inventors have characterized twenty four (24) penicillin tolerant strains (out of 57 clinical isolates and laboratory strains). In order to extend the observation from the NEM316 and 515 strains to the other remaining 23 strains, the inventors used a PCR amplification and sequencing approach.

Primers for PCR amplification were designed based on the sequences (See FIG. 6). The nucleotide sequence and the utility of these two primer pairs are listed in Table 10. Forward primers (PBP4-AP1 and PBP4-AP4) and reverse primers (PBP4-AP2 and PBP4-AP3) were prepared.

TABLE 10

| Primers | Sequence (5' to 3') | Utility |
|---|---|---|
| PBP4-AP1 | 5'-CAGTCGTAACGTTAGTAGC-3' (SEQ ID NO: 1) | Amplify the G503A SNP region producing a 241 bp amplicon. |
| PBP4-AP2 | 5'-CCTATTCGTGAACTGATTAC-3' (SEQ ID NO: 3) | *PBP4-AP2 was used to sequence identify the G168D in PBP4. |
| PBP4-AP3 | 5'-GGTCGGAACTCCTTATGAAG-3' (SEQ ID NO: 4) | Amplify the G865A SNP region producing a 295 bp amplicon. |
| PBP4-AP4 | 5'-GGCTTTTAATACAGGAGTTTTAG-3' (SEQ ID NO: 2) | *PBP4-AP3 was used to sequence identify the V289I in PBP4. |

Example 9

Sequence of G168D and V289I Polymorphisms in GBS Clinical and Laboratory Strains With the primers, the segment of the penicillin binding protein 4 gene was amplified. Table 11 summarizes the SNP (G or D; V or I) and its correlation with the phenotype of GBS clinical and laboratory strains.

TABLE 11

| Clinical GBS Strain # (serotype) | Phenotype | SNP-G or D SNP-V or I |
|---|---|---|
| 12 (III) | S | G-V |
| 18 (NT) | S | G-V |
| 21 (NT) | S | G-V |

TABLE 11-continued

| | | |
|---|---|---|
| 26 (NT) | S | G-V |
| 46 (Ib) | S | G-V |
| 47 (III) | S | G-V |
| 71 (III) | S | G-V |
| 90 (Ib) | S | G-V |
| 91 (III) | S | G-V |
| 93 (Ib) | S | G-V |
| 101 (NT) | S | G-V |
| 122 (III) | S | G-V |
| 129 (V) | S | G-V |
| 131 (V) | S | G-V |
| 172 (NT) | S | G-V |
| 180 (V) | S | G-V |
| 193 (III) | S | G-V |
| 204 (V) | S | G-V |
| 211 (Ib) | S | G-V |
| 244 (Ib) | S | G-V |
| 272 (V) | S | G-V |
| 308 (V) | S | G-V |
| 316 (V) | S | G-V |
| 306 (II) | S | G-V |
| 307 (II) | S | G-V |
| 359 (V) | S | G-V |
| 367 (V) | S | G-V |
| 377 (V) | S | G-V |
| 378 (NT) | S | G-V |
| 379 (V) | S | G-V |
| 388 (NT) | S | D-I |
| A909 (Ia) | S | G-V |
| 2603V/R (V) | S | G-V |
| 68 (III) | PE-PT | G-V |
| 97 (V) | PE-PT | G-V |
| 264 (V) | PE-PT | G-V |
| 268 (Ib) | PE-PT | G-V |
| 273 (V) | PE-PT | G-V |
| 311 (Ib) | PE-PT | G-V |
| 399 (V) | PE-PT | G-V |
| COH1 (III) | PE-PT | G-V |
| 127 (Ia) | PE-PT | D-I |
| 156 (Ia) | PE-PT | D-I |
| 296 (Ia) | PE-PT | D-I |
| 357 (NT) | PE-PT | D-I |
| 380 (NT) | PE-PT | D-I |
| NEM316 (III) | PE-PT | D-I |
| 22 (V) | PT | G-V |
| 279 (III) | PT | G-V |
| 320 (III) | PT | G-V |
| 60 (NT) | PT | D-I |
| 117 (Ia) | PT | D-I |
| 219 (Ia) | PT | D-I |
| 389 (Ia) | PT | D-I |
| 391 (NT) | PT | D-I |
| O90R (NT) | PT | D-I |
| 515 (Ia) | PT | D-I |

"--" indicates an $OD_{600}$ of 0.001 to 0.099
"+" indicates an $OD_{600}$ of 0.100 to 0.250
"++" indicates an $OD_{600}$ of 0.251 to 0.750
"+++" indicates an $OD_{600}$ of 0.751 to 1.500

| Phenotype | Percent (# of isolates) | Strain PBP4 a.a. polymorphisms |
|---|---|---|
| Susceptible | 60.8 (31) | 30 G168/V289; 1 D168/I289 |
| Paradoxical Effect-Penicillin Tolerant | 23.5 (12) | 7 G168/V289; 5 D168/I289 |
| Penicillin Tolerant | 15.7 (8) | 3 G168/V289; 5 D168/I289 |

Thus, in most cases (97%), the inventors deduced amino acid polymorphisms (G168D and V289I) strongly associated with PT (Table 11). The amino acid polymorphisms were deduced based on the SNPs analysis using PCR followed by sequencing.

Upon sequencing the pbp4 gene from 51 clinical GBS isolates, G503A and G865A single nucleotide polymorphism (SNPs), resulting in the G168D and V289I amino acid polymorphisms, respectively, were found in absolute linkage disequilibrium and were associated with 50% of the tolerant strains (Table 11). Interestingly, upon serotype analysis, the tolerant clinical isolates that contain the polymorphisms were found to be either serotype Ia or non-typable (Table 12).

Table 12 depicts the serotype distribution of susceptible (S), paradoxical effect-penicillin tolerant (PE-PT) and penicillin tolerant (PT) clinical GBS isolates. Serotypes Ia were found to be exclusively PT or PE-PT. The tolerant isolates that possess the G168D-V289I PBP4 allele (in bold) were found to be seroptypes 1a or non-typable (NT). The NT Susceptible group contained one G168D-V289I PBP4 allele (bold, +1).

TABLE 12

| GBS Serotype (# of clinical isolates) | Ia (6) | Ib (7) | II (2) | III (9) | V (16) | NT (11) |
|---|---|---|---|---|---|---|
| Susceptible (31) | 0 | 5 | 2 | 6 | 11 | 6 + 1 |
| Paradoxical Effect-PT (12) | 3 | 2 | 0 | 1 | 4 | 2 |
| Penicillin Tolerant (8) | 3 | 0 | 0 | 2 | 1 | 2 |

Example 10

Statistical Analysis of G503A and G865A Single Nucleotide Polymorphisms and Penicillin Tolerance A) Determination of penicillin tolerance with the detection of D and/or I allele for clinical strains: 50% Sensitivity, 97% Specificity, 91% PPV, and 75% NPV.

Fisher's Exact Test

The inventors conducted a statistical analysis (i.e., Fisher's Exact Test) on the 51 clinical isolates. The two-sided P value is 0.0001, considered extremely significant. The row/column association is statistically significant.

TABLE 13

| | Broth Assay PT | Broth Assay S | Total |
|---|---|---|---|
| D168; I289 | 10 (20%) | 1 (2%) | 11 (22%) |
| G168; V289 | 10 (20%) | 30 (59%) | 40 (78%) |
| Total | 20 (39%) | 31 (61%) | 51 (100%) |

TABLE 14

| Variable | Value | 95% Confidence Interval |
|---|---|---|
| Sensitivity | 0.5000 | 0.2720 to 0.7280 |
| Specificity | 0.9677 | 0.8332 to 0.9992 |
| Positive Predictive Value | 0.9091 | 0.5874 to 0.9977 |
| Negative Predictive Value | 0.7500 | 0.5881 to 0.8733 |
| Likelihood Ratio | 15.500 | |

Therefore, the amino acid polymorphisms correlate highly with the penicillin tolerance assay; with a sensitivity value of 0.5 and a specificity value of 0.9677. Notably, the present SNP assay provides a high specificity in detecting penicillin tolerance in Group B *Streptococcus*.

B) Determination of penicillin tolerance with the detection of D and/or I allele for clinical and laboratory strains: 54% Sensitivity, 97% Specificity, 93% PPV, and 74% NPV.

In this study, the inventors further examined using the Fisher's Exact Test and included all the strains (i.e., 51 clinical isolates and 6 laboratory strains).

TABLE 15

|  | Broth Assay PT | Broth Assay S | Total |
|---|---|---|---|
| D168; I289 | 13 (23%) | 1 (2%) | 14 (25%) |
| G168; V289 | 11 (19%) | 32 (56%) | 43 (75%) |
| Total | 24 (42%) | 33 (58%) | 57 (100%) |

TABLE 16

| Variable | Value | 95% Confidence Interval |
|---|---|---|
| Sensitivity | 0.5417 | 0.3285 to 0.7448 |
| Specificity | 0.9697 | 0.8423 to 0.9992 |
| Positive Predictive Value | 0.9286 | 0.6611 to 0.9982 |
| Negative Predictive Value | 0.7442 | 0.5887 to 0.8646 |
| Likelihood Ratio | 17.875 | |

Thus, when all the strains were analyzed, the same high degree of specificity value (i.e., 0.9697) was found. Together, these data indicate that the present SNP assay is extremely specific to predict if a pregnant woman is colonized with penicillin tolerant Group B *Streptococci*.

Example 11

Primers and Probes Used for Determination of Presence of a SNP

In this example, primers and probes were selected to determine the presence of a G503A SNP.

FIG. 7 depicts the nucleotide sequence for penicillin binding protein 4 (*Streptococcus agalactiae* NEM 316). FIG. 7 also depicts primers within the nucleotide sequence that may be used to determine the presence of a G503A SNP. In particular, the following primers or various combinations of the following forward and reverse primers may be used in determining the presence of a G503A SNP using PCR:

TABLE 17

| Primer Name | Primer sequence 5' to 3' | SEQ ID NO. | Amplicon[1] | Tm[2] |
|---|---|---|---|---|
| Forward Primers: | | | | |
| PBP4-F1 | TTGCTTATCCTATTCGTGAACTG | SEQ ID NO: 5 | 240 bp | 52.8 |
| PBP4-F2 | CTGTCCCGTCATCTAATGT | SEQ ID NO: 6 | 236 bp | 51.4 |
| PBP4-F3 | GTCCCGTCATCTAATGTAGCA | SEQ ID NO: 7 | 177 bp | 54.1 |
| PBP4-F4 | CAATCCTGACGCCTTCATT | SEQ ID NO: 8 | 156 bp | 52.9 |
| Reverse Primers: | | | | |
| PBP4-R1 | CGTTAGTAGCATTGTTATCGTATTC | SEQ ID NO: 9 | | 51.8 |
| PBP4-R2 | GTCGTAACGTTAGTAGCATTGT | SEQ ID NO: 10 | | 52.7 |
| PBP4-R3 | CTTTTGGGGAGTAAAGTCCATTAA | SEQ ID NO: 11 | | 53.0 |
| PBP4-R4 | GGTTAAAATTGATAGATCACGTGC | SEQ ID NO: 12 | | 52.4 |

[1]Amplicon size in base pairs (bp) for F2/R2, F3/R3, F4/R4 primer pairs.
[2]Calculated primer melting temperature in ° C.

One of ordinary skill in the art would optimize primers and probes, using the details described above, to determine the presence of SNP G865A.

Example embodiments include one set of primers and at least two probes in the same reaction. By way of non-limiting example, at least one HEX channel probe and at least one FAM Channel probe may be used, where the HEX channel probe detects penicillin tolerance, and the FAM channel probe detects penicillin susceptibility. Example HEX and FAM channel probes are provided below:

TABLE 18

Penicillin Tolerance Assay Duplex Probes

| Probe Name | Primer sequence 5' to 3'[1] | SEQ ID NO. | Tm[2] |
|---|---|---|---|
| *HEX Channel for Penicillin Tolerance Probes Forward (FPr) and Reverse Complement (RCPr)* | | | |
| PBP4-PT-FPr | CGCCAAGAAACTCGATATGACAAA | SEQ ID NO: 13 | 55.6 |
| PBP4-PT-RCPr | TTTGTCATATCGAGTTTCTTGGCG | SEQ ID NO: 14 | 55.6 |
| *FAM Channel for Penicillin Susceptible Probes Forward (FPr) and Reverse Complement (RCPr)* | | | |
| PBP4-S-FPr | GCCAAGAAACTCGGTATGACAAA | SEQ ID NO: 15 | 55.6 |
| PBP4-S-RCPr | TTTGTCATACCGAGTTTCTTGGC | SEQ ID NO: 16 | 55.6 |

[1]Highlighted nucleotide is the G503A SNP. Beacon probe stem sequence not shown.
[2]Calculated primer melting temperature in ° C.

As shown above, the HEX channel probe (SEQ ID NO: 13) is shifted one nucleotide from the FAM Channel probe (thus, beginning with the nucleotide "C", rather than at the "G") so as to change the anneal temperature of the HEX channel probe to essentially match the anneal temperature of the FAM channel probe. Other than this shift the HEX and FAM probes essentially correspond to each other than at the location of a SNP to be detected, which is underlined.

According to alternative embodiments, the following CAMP primers and probes may be used:

TABLE 19

| Primer Name | Primer sequence 5' to 3' | SEQ ID NO. |
|---|---|---|
| CAMP Forward | CTGGAACTCTAGTGGCTGGT | SEQ ID NO: 17 |
| CAMP Reverse | CATTTGCTGGGCTTGATTATTACT | SEQ ID NO: 18 |
| Probe Name | | |
| CAMP Probe | AGTGACAACTCCACAA | SEQ ID NO: 19 |

[1]Beacon probe stem sequence not shown.

Example 11

The Effects of pbp4 Allele Replacement in A909 and O90R on Membrane Permeability, Cell Viability, and Cell Wall Integrity These SNPs in pbp4 represent excellent molecular biomarkers for tolerance in GBS. In order to ascertain whether these PBP4 polymorphisms render a functional role in tolerance as well, an allele replacement experiment was performed. The pbp4 gene was amplified by PCR using primers Pbp4AR-F and Pbp4AR-R (Table 20) and cloned into the pVE6007ts integration vector. The pVE6007ts-pbp4 vector was used to transform GBS and integrate a PT (DI) or S (GV) pbp4 allele behind the endogenous promoter at the endogenous pbp4 locus in A909 (S) and O90R (PT) by single crossover recombination. PCR, using primers Pbp4-Intg and pVE-CM1 (Table 20), was used to determine accurate integration into the genome of the transformed GBS strains. To make sure that the plasmid integration did not alter the phenotype, the endogenous S and PT pbp4 allele was integrated in the S and PT strains, respectively. Furthermore, the pbp4 integration is non-polar, since no downstream genes were identified. The macrobroth PKR assay was performed on A909-GV, A909-DI, O90R-DI and O90R-GV integration strains. The allele replaced A909-DI and O90R-GV strains showed a clear change in phenotype from S to PT and from PT to PE-PT, respectively, while the A909-GV and O90R-DI controls remained unchanged (data not shown). Since the PKR assays are only designed to provide a positive (growth) or negative (no growth) result, determining phenotypic changes upon genetic manipulation becomes difficult. For example, post-penicillin treated regrowth cultures can differentiate between 0 and ≧1 viable cell but cannot differentiate 1 versus 10,000 viable cells. In order to obtain a more quantitative measure of the phenotypic alterations, PI and RSG viability staining assays were performed (FIGS. 8a and 8b). A909-DI cells showed a significant decrease in PI membrane permeability and an increase in RSG cell viability staining compared to the A909 (parent), while O90R-GV showed a significant increase in PI membrane permeability and a decrease RSG cell viability staining compared to the O90R (parent), further validating the results shown by the PKR assays. The control strains A909-GV and O90R-DI did not show a significant change in PI and RSG fluorescence as compared to their respective parent strains, discounting any role by the plasmid vector in phenotype alterations.

TABLE 20

| Primer Name | Primer sequence 5' to 3' | SEQ ID NO. |
|---|---|---|
| Pbp4AR-F | CAAGAGATAATAAAAAGCC | SEQ ID NO: 20 |
| Pbp4AR-R | TAACCTAAATTAATCGTATCTTTCC | SEQ ID NO: 21 |
| Pbp4-Intg | GAATTACCAATGGAATATGCGG | SEQ ID NO: 22 |
| pVE-CM1 | CAGATAGGCCTAATGACTGG | SEQ ID NO: 23 |

PBP4, a D-alanyl-D-alanine carboxypeptidase, controls the extent of peptidoglycan cross-linking by clipping the terminal D-Ala, catalyzing transpeptidation. Therefore, the G168D and V289I AAPs of tolerant PBP4 may result in a higher degree of cross-linking thus making the cell more resistant to autolysins, which could contribute to the tolerance phenotype. A survival assay was performed on the parent, allele replaced, and integration control strains. Cells were digested with peptidoglycan digestive enzymes, lysozyme and mutanolysin, for up to 120 minutes and samples taken from different time points were plated for colony counts (FIG. 9). O90R (PT), A909-DI, and O90R-DI strains showed a significant increase in survival compared to A909 (S), O90R-GV, and A909-GV strains. NEM316 (PE-PT) showed a moderate or intermediate level of survival compared to A909 and O90R (data not shown). These data suggest that the cell walls of PT strains are more resistant to enzymatic digestion potentially due to an increase in peptidoglycan cross-linking. Furthermore, these observations indicate that the pbp4 DI allele plays a central role in the cell wall integrity of tolerant strains.

Differences in the peptidoglycan structural integrity between S and PT strains were further investigated, which may allude to the amount of cross-linking. The peptidoglycan layer of GBS strains was isolated at early-exponential phase, digested with lysozyme and mutanolysin, and the peptidoglycan muropeptides were separated by SDS-PAGE (FIG. 10). Throughout this experiment, it was noted that the peptidoglycan of the PT strains were significantly more difficult to extract and more resistance to cell wall disruption (data not shown). Results revealed that the O90R parent (PT) and the O90R-DI allele replacement control (PT) showed a HMW 250 kDa and a major LMW 14 kDa peptide bands that are absent in the A909 parent (S) and the A909-GV allele replacement control (S).

Upon replacing the pbp4-GV to pbp4-DI allele in A909 and the pbp4-DI to pbp4-GV allele in O90R, the peptidebanding pattern switched. The A909-DI strain now showed a diffuse 250 kDa and a major 14 kDa peptide bands, similar to the O90R parent. Whereas the O90R-GV strain demonstrated a banding pattern similar to the A909 parent. This suggests that strains with the pbp4-DI allele generate a cell wall more resistant to lytic enzymes as demonstrated by the HMW 250 kDa peptidoglycan muropeptide complex not found in S strains after digestion. Furthermore, the pbp4-DI allele produced a characteristic digestion pattern independent of a strain's genetic background. Similar results were reported by Zhou et al. upon comparing size and complexity differences of the peptidoglycan digested muropeptides in β-lactam resistant and susceptible Staphylococcal strains. These results demonstrate that the pbp4-DI allele alters the peptidoglycan structure, perhaps by an increase in the peptidoglycan cross-linking activity, producing a more durable sacculus and an increase in cell wall integrity.

Experimental Protocols (I) Bacterial Strains and Culture Conditions. GBS strains A909 (serotype IA), 515 (serotype IA), NEM316 (serotype III), COHI (serotype III), 2603V/R (serotype V) and O90R (non-typable) were used in this study. *E. coli* Top10 cells were used for the recombination experiments. GBS was cultured in Todd Hewitt broth (THB) or Tryptic Soy 5% sheep blood (TS) media and *E. coli* in Luria-broth (LB) medium or agar. Antibiotics were used at the following concentrations: for GBS—penicillin G ($MIC_{90}$ 0.06 μg ml$^{-1}$), ampicillin ($MIC_{90}$ 0.12 μg ml$^{-1}$), vancomycin ($MIC_{90}$ 2 μg ml$^{-1}$), cefazolin ($MIC_{90}$ 1 μg ml$^{-1}$) and chloramphenicol (5 μg ml$^{-1}$); for *E. coli*—ampicillin (50 μg ml$^{-1}$) and chloramphenicol (5 μg ml$^{-1}$). Both GBS and *E. coli* cultures were grown at 37° C.

(II) Tolerance Using the MBC:MIC Ratio Method. Three GBS laboratory strains (i.e., A909, NEM316, and O90R) were cultured overnight for 18 h at 37° C. in THB. Subcultures in THB were subsequently grown to exponential phase ($OD_{600}$~0.3; i.e. 5×10$^5$ cfu/ml) at 37° C. Cell cultures were then exposed to different concentrations of antibiotics (Penicillin G, Ampicillin, Cefozolin or Vancomycin). The concentrations chosen were from 0.25×$MIC_{90}$ to 512×$MIC_{90}$ for a time duration of 48 h at 37° C. Cell cultures were dispersed every 18 h before $OD_{600}$ was measured to determine the lowest concentration of antibiotic with 90% growth inhibition ($MIC_{90}$). Antibiotic treated cells (8 μl) from each well were re-suspended into PBS (100 μl) and plated (54 μl) on TS agar plates and allowed to grow for an additional 24 h at 37° C. Cell count was performed to determine the lowest concentration of antibiotic with 90% killing of original inoculums ($MBC_{90}$).

(III) Penicillin Killing and Regrowth Tolerance Assay by Microbroth Dilution. Three GBS laboratory strains (i.e., A909, NEM316, and O90R) were cultured overnight for 18 h at 37° C. in THB. Subcultures in THB were subsequently grown to exponential phase ($OD_{600}$~0.3) at 37° C. Cell cultures were then exposed to different concentrations of Penicillin G (Sigma, St. Louis, Mo.). The concentrations chosen were from 0.06 μg ml$^{-1}$ to 15.4 μg ml$^{-1}$ (which correspond to 1×$MIC_{90}$ to 256×$MIC_{90}$; MIC refers to minimal inhibition concentrations that inhibits 90% of cells) for a time duration of 48 h at 37° C. Cell cultures were dispersed. A 1:20 dilution of cells was re-plated into new wells containing fresh THB with 500 U Penase (to degrade residual penicillin). Cell cultures were allowed to re-grow for an additional 24 h at 37° C. before the $OD_{600}$ was measured.

(IV) Measuring Cell Viability by Determining ATP Concentration. GBS strains were cultured for 18 h at 37° C. in THB. These cells were inoculated into fresh THB and subsequently allowed to grow to exponential phase ($OD_{600}$ 0.25-0.3) at 37° C. One ml of each culture was centrifuged at 5,000×g for 4 min. The cell pellet was re-suspended in ATP-free water. Cellular ATP was extracted using trichloroacetic acid (TCA) (5%) for 2 min and subsequently neutralized with Tris-EDTA-0.1M NaOAc, pH 7.75 to 10×TCA volume. The initial (in.) cellular ATP concentration ([ATP]) was measured using the ENLITEN (Promega) luciferase based reaction kit. THB cultures were then treated with 100×$MIC_{90}$ Penicillin G for 22 h. The experimental (exp.) cellular ATP was extracted and the concentration was measured as stated above. Based on the calculations ([ATP] exp.)/([ATP] in./O.D. in.), differences in viability were equated with the change in [ATP].

(V) Measuring Penicillin Induced Lysis. Three GBS laboratory strains (A909, NEM316, and O90R) were cultured for 18 h at 37° C. in THB. Subcultures in THB were subsequently grown to exponential phase ($OD_{600}$~0.3) at 37° C. Cells were treated with 100×$MIC_{90}$ Penicillin G for an additional 22 h. $OD_{600}$ of these cell cultures before (OD initial) and after penicillin treatment (OD experimental) was measured (N=3). The values of OD experimental were subtracted from OD initial.

(VI) Penicillin Killing and Regrowth Tolerance Assay by Macrobroth Dilution. In this macrobroth culture format, 25 ml THB broth GBS cultures (containing clinical isolates) were grown to an early exponential growth phase (~0.2 $OD_{600}$). Cell cultures (6 ml) were collected and divided into 4 culture tubes. Penicillin G (10, 30, 100, and 300×$MIC_{90}$) were added to these cells and further incubated for 48 h at 37° C. Cell cultures were shaken at 150 rpm in order to maintain cells in suspension for proper growth. Subcultures (1:20 dilution) of cells were put into fresh THB containing 250 U Penase (i.e., 100 μl of Penase 10,000 U stock into 4 ml THB culture). Subcultures were allowed to grow for 24 h at 37° C. Cell growth was monitored by $OD_{600}$.

(VII) Genetic Techniques and DNA Manipulations. Genomic GBS DNA was isolated using a modified version of Gentra® Puregene® Cell Kit protocol: 1.5 μl of lytic enzyme solution [lysozyme (5 μl)+mutanolysin (1 μl)] was added and incubated at 37° C. for 30 minutes before adding cell lysis solution. Standard recombinant DNA techniques were used for nucleic acid preparation and analysis. Plasmid DNA was prepared using SV Promega's plasmid extraction kit. Primer sequences (Table 10) were based on the published genome of GBS strain A909 (GenBank CP00114). Primer pair AP1 and AP2 was used to amplify and sequence 241 bp of G503A SNP region in pbp4 gene. Primers AP3 and AP4 were used to amplify and sequence 295 bp of G865A SNP region in pbp4 gene. PCR was carried out with USB Taq polymerase as advised by manufacturer. Amplification products were purified using SV Promega's gel cleanup kit and sequenced using Applied Biosystems 3130 Genetic Analyzer. Recombinant plasmid DNA was introduced into *E. coli* using chemical transformation. Electrocompetent GBS cells were prepared and transformed as described previously.

(VII) Construction of Bacterial Strains. Allele replacement experiments were performed with the construction of GBS strains A909-GV, A909-DI, O90R-DI and O90R-GV by replacing the opposing pbp4 gene in a susceptible (A909) and tolerant (O90R) laboratory strain. The pbp4 gene was amplified from both A909 and O90R genome using primer set Pbp4AR-F and Pbp4AR-R. The resulting PCR product was cloned into TOPO vector and transformed into *E. coli* (Top10) cells using TOPO TA Cloning® kit (Invitrogen). The transformants were selected from LB+ Amp plates. The Topo plasmid constructs were digested with Bam HI (Promega) and Xba I (Promega) and pbp4 insert was purified using SV PCR CLEAN UP KIT (Promega). Plasmid constructs pVE6007-pbp4-GV and pVE6007-pbp4-DI were made by ligating Bam HI and Xba I digested pVE6007ts (temperature sensitive origin of replication plasmid, maintained at the permissive temperature of 30° C. in Top10 cells) with Bam HI and Xba I digested pbp4-GV (A909) and pbp4-DI (O90R) using USB's T4 ligase. The pVE6007-pbp4 constructs were transformed into Top10 cells and selected on LB with 5 μg ml$^{-1}$ chloramphenicol agar plates after an overnight growth at 30° C. The pVE6007-pbp4 constructs were transformed using electroporation into respective GBS strains and the transformed cells were selected on TS with 5 μg ml$^{-1}$ chloramphenicol agar plates at the permissive 30° C. Transformants were serial cultured at the restrictive temperature of 37° C. to select colonies that have undergone a plasmid recombination event within the genome and eliminate autonomous plasmids. Stable 37° C. transformants were confirmed using PCR followed by sequencing. Primer pair Pbp4-Intg and pVE-CM1 was used to confirm the genome integration of pVE6007-pbp4-GV or pVE6007-pbp4-DI constructs to their respective endogenous loci by PCR. pVE-CM1 was used to sequence the pVE6007-pbp4-GV and pVE6007-pbp4-DI integration sites from genomic DNA.

(IX) Viability Assay Using FACS Analysis. Cells [A909-DI and O90R-GV (experimental) or A909-GV and O90R-DI (control) allele replacement and GBS clinical isolates] were grown to an $OD_{600}$ of 0.25 (early log phase) followed by penicillin treatment (100×MIC) for 48 h. Cells are stained with 0.25 µM RedoxSensor Green (RSG) and 10 µM Propidium iodide (PI) and fixed in 4% PBS with paraformaldehyde prior to measuring the mean fluorescence intensities of RSG and PI by FACS using a BD FACSCalibur® cell sorter. 50,000 individual events were used for the calculation of the geometric mean of RSG or PI fluorescence intensity. Fluorescence intensity of the RSG stain, which is an indicator of bacterial reductase activity, was used to measure cell viability whereas extent of membrane permeability/damage was determined by staining with membrane-impermeable PI.

(X) Survival Assay. Percentage survival of A909, NEM316 and O90R was measured after treatment of log phase cells with lysozyme and mutanolysin (final enzyme concentration 5 µg ml$^{-1}$ of each) for 0, 30, 60, 90 and 120 min at 37° C. 100 µl aliquots were taken at each time point, serially diluted, plated on TSB plates and incubated overnight at 37° C. Surviving colonies were counted and expressed as a percentage of the untreated cells plated at 0 min.

(XI) Peptidoglycan Cross-Linkage Estimation By Analysis Of Muropeptides. Cells were harvested (6000×g, 10 min) from 1 L of an exponentially growing culture ($OD_{600}$~0.3) and washed in 50 mM sodium phosphate (pH 6.5) at 4° C., and re-suspended in 1 M NaCl. The cells were disrupted and the cell wall fraction collected as described by de Jonge et al., 1992 with some modifications. Cell walls were digested with trypsin (1 mg/ml, at 37° C., for 16 h) to remove covalently bound cell wall protein. The enzyme was inactivated by boiling for 15 min in 1% SDS. The residual walls were sedimented, washed repeatedly 3× with water, and freeze-dried by dry-ice EtOH bath and 4° C. speed vac for 18 h. Peptidoglycan (1 mg/ml) was digested in 12.5 mM phosphate buffer (pH 5.5) with lysozyme and mutanolysin (final enzyme concentration 5 µg/ml of each). Samples at a final volume of 500 µl were incubated for 16 h at 37° C. and subsequently boiled for 5 min and centrifuged for 5 min. The digested peptidoglycan was re-dissolved in 50 mM sodium acetate buffer (pH 4.9) and subsequently flash frozen in a dry-ice and ethanol mixture. The solubilized peptidoglycan fragments were then dried by rotary evaporation and resuspended in filtered ddH$_2$O just prior to electrophoretic separation. Samples (15 µg) were mixed with sample buffer and boiled for 5 minutes before loading on a 16.5% Tris-Cl peptide gel and run at a constant voltage of 100 V using 1× Tris-Tricine-SDS gel running buffer. The peptide bands obtained were stained with BioSafe Coomassie stain.

(XII) Statistical Analysis. Data are expressed as a mean plus and minus standard deviation. Statistical analyses were performed using the Student's t-test and sensitivity and specificity were calculated using a two-tailed Fishers Exact test. Values were considered statistically significant at p<0.05.

Although the invention has been described in example embodiments, additional modifications and variations would be apparent to those skilled in the art. It is therefore to be understood that the inventions herein may be practiced other than as specifically described. Thus, the present embodiments should be considered in all respects as illustrative and not restrictive. Accordingly, it is intended that such changes and modifications fall within the scope of the present invention as defined by the claims appended hereto.

---

What is claimed is:

1. A method of detecting penicillin tolerance in Group B *Streptococcus*, comprising:
   (a) providing a biological sample; and
   (b) detecting at least one single nucleotide polymorphism (SNP) in penicillin binding protein 4 in said biological sample, wherein said SNP is selected from the group consisting of G503A and G865A, and wherein the presence of said SNP is indicative of penicillin tolerance in Group B *Streptococcus*.

2. The method of claim 1, wherein said biological sample is selected from the group consisting of a cervicovaginal swab, rectal swab, whole blood, urine, cerebrospinal fluid, and ascites fluid.

3. The method of claim 1, wherein the detecting step is performed by a PCR technology selected from the group consisting of real-time PCR, pyrosequencing, and conventional PCR followed by sequencing.

4. The method of claim 1, wherein the detecting step is performed by real-time PCR.

5. The method of claim 4, wherein said real-time PCR is performed using a primer set comprising:
   (a) at least one forward primer selected from the group consisting of a nucleotide sequence of SEQ ID NO: 5, SEQ ID NO: 6, SEQ ID NO: 7, SEQ ID NO: 8, and SEQ ID NO:17; and
   (b) at least one reverse primer selected from the group consisting of a nucleotide sequence of SEQ ID NO: 9, SEQ ID NO: 10, SEQ ID NO: 11, SEQ ID NO: 12, and SEQ ID NO: 18.

6. The method of claim 4, wherein said real-time PCR is performed using at least one isolated hybridization probe comprising at least one nucleotide sequence selected from the group consisting of SEQ ID NO: 13, SEQ ID NO: 14, SEQ ID NO: 15, SEQ ID NO: 16, and SEQ ID NO: 19.

7. The method of claim 4, wherein said real-time PCR is performed at an annealing temperature of about 58° C. to about 60° C.

8. The method of claim 4, wherein said real-time PCR is performed with an annealing time of about 30 seconds to about 60 seconds.

9. The method of claim 4, wherein said detecting step utilizes molecular beacon technology with a specific primer set to detect at least one SNP in penicillin binding protein 4 selected from the group consisting of G503A and G865A.

10. The method of claim 1, wherein said detecting step is performed by pyrosequencing.

11. The method of claim 1, wherein said detecting step comprises conventional PCR followed by sequencing.

12. The method of claim 11, wherein said conventional PCR is performed using a primer set, wherein said primer set is specific for at least one single nucleotide polymorphism in penicillin binding protein 4 selected from the group consisting of G503A and G865A.

13. The method of claim 12, wherein said primer set specific for G503A comprising:
   (a) at least one forward primer having a nucleotide sequence of SEQ ID NO: 1; and
   (b) at least one reverse primer having a nucleotide sequence of SEQ ID NO: 3.

14. The method of claim 12, wherein said primer set specific for G865A comprising:
   (a) at least one forward primer having a nucleotide sequence of SEQ ID NO: 2; and (b) at least one reverse primer having a nucleotide sequence of SEQ ID NO: 4.

15. The method of claim 1, further comprising (c) detecting Group B *Streptococcus* using at least one primer set against a Group B *Streptococcus*-specific gene, wherein presence of said *Streptococcus*-specific gene is indicative of the presence of Group B *Streptococcus*.

16. The method of claim 15, wherein said detecting step (b) and said detecting step (c) are performed substantially simultaneously.

17. The method of claim 15, wherein said detecting step (b) and said detecting step (c) are performed sequentially.

18. The method of claim 15, wherein said Group B *Streptococcus*-specific gene is CAMP factor.

19. A set of isolated oligonucleotides comprising a forward primer, a reverse primer and a hybridization probe, wherein said forward primer having a nucleotide sequence selected from the group consisting of SEQ ID NO: 1, SEQ ID NO: 2, SEQ ID NO: 3, and SEQ ID NO: 4, said reverse primer having a nucleotide sequence selected from the group consisting of SEQ ID NO: 5, SEQ ID NO: 6, SEQ ID NO: 7, SEQ ID NO: 8, SEQ ID NO: 17, SEQ ID NO: 9, SEQ ID NO: 10, SEQ ID NO: 11, and SEQ ID NO: 12, and SEQ ID NO: 18, and said hybridization probe having a nucleotide sequence selected from the group consisting of SEQ ID NO: 13, SEQ ID NO: 14, SEQ ID NO: 15, SEQ ID NO: 16, and SEQ ID NO: 19.

20. A method of diagnosing penicillin tolerance in a mammal, comprising:
  (a) providing a biological sample from a mammal;
  (b) detecting at least one single nucleotide polymorphism (SNP) in penicillin binding protein 4 in said biological sample, wherein said SNP is selected from the group consisting of G503A and G865A; and
  (c) correlating presence of said SNP to penicillin tolerance in Group B *Streptococcus*.

21. The method of claim 20, wherein the mammal is a human.

22. The method of claim 20, wherein if said mammal is diagnosed positive for penicillin tolerance, the method further comprises administering a non-penicillin antibiotic to said mammal.

23. A kit for detecting penicillin tolerance in Group B *Streptococcus*, comprising:
  (a) at least one primer set capable of detecting at least one single nucleotide polymorphism (SNP) in penicillin binding protein 4 in a biological sample, wherein said SNP is selected from the group consisting of G503A and G865A;
  b) at least one hybridization probe capable of detecting at least one SNP in penicillin binding protein 4 in a biological sample, wherein said SNP is selected from the group consisting of G503A and G865A; and
  c) an instruction for using said primer set to detect said at least one SNP.

24. The kit of claim 23, wherein said instruction provides guidance to use said primer set and said hybridization probe in performing real-time PCR in detecting penicillin tolerance in Group B *Streptococcus* in a biological sample.

25. The kit of claim 23, wherein said primer set contains a forward primer and a reverse primer, wherein said forward primer having a nucleotide sequence selected from the group consisting of SEQ ID NO:5, SEQ ID NO: 6, SEQ ID NO: 7, SEQ ID NO: 8, and SEQ ID NO: 17, and wherein said reverse primer having a nucleotide sequence selected from the group consisting of SEQ ID NO:9, SEQ ID NO:10, SEQ ID NO:11, SEQ ID NO:12, and SEQ ID NO:18.

26. The kit of claim 23, wherein said instruction provides guidance to use said primer set in performing conventional PCR followed by sequencing in detecting penicillin tolerance in Group B *Streptococcus* in a biological sample.

27. The kit of claim 23, wherein said primer set contains a forward primer and a reverse primer, wherein said forward primer having a nucleotide sequence selected from the group consisting of SEQ ID NO:1, and SEQ ID NO: 2, and wherein said reverse primer having a nucleotide sequence selected from the group consisting of SEQ ID NO: 3, and SEQ ID NO: 4.

\* \* \* \* \*